United States Patent [19]
Buechler et al.

[11] Patent Number: 5,679,526
[45] Date of Patent: *Oct. 21, 1997

[54] THRESHOLD LIGAND-RECEPTOR ASSAY

[75] Inventors: Kenneth F. Buechler, San Diego; Gunars E. Valkirs, Escondido; Richard R. Anderson, Encinitas, all of Calif.

[73] Assignee: Biosite Diagnostics Incorporated, San Diego, Calif.

[*] Notice: The term of this patent shall not extend beyond the expiration date of Pat. Nos. 5,028,535 and 5,089,391.

[21] Appl. No.: 284,035

[22] Filed: Aug. 1, 1994

Related U.S. Application Data

[63] Continuation of Ser. No. 832,865, Feb. 6, 1992, abandoned, and Ser. No. 463,150, Jan. 10, 1990, Pat. No. 5,089,391, which is a continuation-in-part of Ser. No. 295,568, Jan. 10, 1989, Pat. No. 5,028,535.

[51] Int. Cl.⁶ ..................................... C01N 33/53
[52] U.S. Cl. ............... 435/7.1; 435/7.5; 435/7.9; 435/7.92; 435/7.93; 435/7.94; 435/805; 435/810; 435/967; 436/501; 436/514; 436/518; 436/524; 436/525; 436/526; 436/810; 436/825
[58] Field of Search ............... 435/7, 7.1, 7.92–7.95, 435/805, 810, 967; 436/517, 805, 807, 501, 514, 518, 524–539, 810, 824, 825; 422/56–58, 61

[56] References Cited

U.S. PATENT DOCUMENTS

| | | |
|---|---|---|
| 3,654,090 | 4/1972 | Schuurs et al. |
| 3,817,837 | 6/1974 | Rubenstein et al. |
| 3,878,187 | 4/1975 | Schneider et al. |

(List continued on next page.)

FOREIGN PATENT DOCUMENTS

| | | |
|---|---|---|
| 0203238 | 12/1986 | European Pat. Off. |
| 0253464 | 1/1988 | European Pat. Off. |
| 0267006 | 5/1988 | European Pat. Off. |
| 2171999 | 9/1986 | United Kingdom. |
| 8606170 | 10/1986 | WIPO. |

OTHER PUBLICATIONS

Lee, S. & & Liberti, P.A., *Analytical Biochem.*, 166:41–48 (1987).

Ekins, R.P., et al., "Theoretical Aspects of Saturation and Radio Immunoassay" in Radioiostopes in Medicine: In Vitro Studies (Goswitz & Murphy eds.) U.S. Atomic Energy Comm'n, Oak Ridge, TN,9–100 (1968).

(List continued on next page.)

*Primary Examiner*—Paula K. Hutzell
*Assistant Examiner*—Rachel Heather Freed
*Attorney, Agent, or Firm*—Lyon & Lyon LLP

[57] ABSTRACT

This invention is directed to a ligand-receptor assay for determining the presence of at least one target ligand, capable of competing with a ligand analogue conjugate for binding sites available on a ligand receptor, said ligand analogue conjugate comprising at least one ligand analogue coupled to a colloidal gold particle, in a fluid sample suspected of containing said target ligand comprising the steps of:

a. contacting said fluid sample with said ligand analogue conjugate and said ligand receptor to form a homogeneous reaction mixture, the relative amounts of said ligand analogue conjugate and said ligand receptor being selected such that in the absence of said target ligand and subsequent to substantially equilibrium binding in said reaction mixture, substantially all of said ligand analogue conjugate is bound to said ligand receptor such that no unbound ligand analogue conjugate is detected as a result of the assay method;

b. detecting unbound ligand analogue conjugates in said reaction mixture by visual means using at least one ligand receptor immobilized on a solid phase in at least one distinct locus;

c. relating the detectable signal to the presence of said target ligand in said fluid sample.

4 Claims, 8 Drawing Sheets

U.S. PATENT DOCUMENTS

| | | |
|---|---|---|
| 3,884,898 | 5/1975 | Schneider . |
| 4,125,372 | 11/1978 | Kawai et al. . |
| 4,168,146 | 9/1979 | Grubb et al. . |
| 4,200,690 | 4/1980 | Root et al. . |
| 4,203,802 | 5/1980 | Rubenstein et al. . |
| 4,233,402 | 11/1980 | Maggio et al. . |
| 4,246,339 | 1/1981 | Cole et al. . |
| 4,281,065 | 7/1981 | Lin et al. . |
| 4,298,685 | 11/1981 | Parikh et al. . |
| 4,313,734 | 2/1982 | Leuvering ................................. 422/61 |
| 4,358,535 | 11/1982 | Falkow et al. . |
| 4,366,241 | 12/1982 | Tom et al. . |
| 4,391,904 | 7/1983 | Litman et al. . |
| 4,425,438 | 1/1984 | Bauman et al. . |
| 4,435,504 | 3/1984 | Zuk et al. . |
| 4,446,232 | 5/1984 | Liotta . |
| 4,477,576 | 10/1984 | Deutsch et al. . |
| 4,496,654 | 1/1985 | Katz et al. . |
| 4,506,009 | 3/1985 | Lenhoff et al. . |
| 4,540,659 | 9/1985 | Litman et al. . |
| 4,632,901 | 12/1986 | Valkirs et al. . |
| 4,727,019 | 2/1988 | Valkirs et al. . |
| 4,740,468 | 4/1988 | Weng et al. . |
| 4,828,985 | 5/1989 | Self . |

OTHER PUBLICATIONS

Rodgers, R., et al., *Clin. Chem.* 24:95–100 (1976).

Liu, D., et al., *Clin. Toxicology,* 25:527–538 (1987).

Pluska, M.G., et al., *BioTechniques,* 4:272–283 (1986).

Zettner, A., *Clin. Chem.* 19:699–705 (1973).

Yalow, R.S. & Berson, S.A., "General Principles of Radio Immunoassay" in Radioisotopes in Medicine: In Vitro Studies (Goswitz & Murphy eds.), U.S. Atomic Energy Comm'n, Oak Ridge, TN 7–41 (1968).

THRESHOLD LIGAND-RECEPTOR ASSAY

This application is a continuation of U.S. application Ser. No. 07/832,865, filed Feb. 6, 1992 (abandoned), and a continuation of U.S. application Ser. No. 07/463,150, filed Jan. 10, 1990 and issued as U.S. Pat. No. 5,089,391 on Feb. 18, 1992, which is a continuation in part of Ser. No. 07/295,568 filed Jan. 10, 1989 and issued as U.S. Pat. No. 5,028,535, which are hereby incorporated by reference and from which priority is claimed.

FIELD OF THE INVENTION

This invention is in the field of ligand-receptor assays, including immunoassays, for the detection of selected analytes in a fluid sample. More particularly, this invention relates to methods for providing thresholds for signal production that are related to ligand concentrations in ligand-receptor assays. The inventive assays herein described may be used to obtain semiquantitative and quantitative determinations of one or more target ligand(s) in a single test format without the need for signal detection instrumentation. The present invention also relates to methods that enable the quantitation of ligand concentrations in samples using a single calibration point with the aid of an instrument. In these assay formats, the intensity of a signal is directly related to ligand concentration in the sample.

BACKGROUND OF THE INVENTION

As used herein, the term "ligand-receptor" assay refers to an assay for an analyte which may be detected by the formation of a complex between a ligand and another substance capable of specific interaction with that ligand, i.e., ligand receptor. The ligand may be the analyte itself or a substance which, if detected, can be used to infer the presence of the analyte in a sample. In the context of the present invention, the term "ligand", includes haptens, hormones, antigens, antibodies, deoxyribonucleic acid (DNA), ribonucleic acids (RNA), metabolites of the aforementioned materials and other substances of either natural or synthetic origin which may be of diagnostic interest and have a specific binding partner therefor, i.e., the ligand receptor of the ligand-receptor assay. In the context of the present invention the term "ligand receptor" includes materials for which there is a specific binding partner, i.e., the ligand of the ligand-receptor assay. Those skilled in the art will appreciate that the analyte of interest, a member of a specific binding pair may be either ligand receptor or ligand depending upon assay design.

Ligand-receptor assays are generally useful for the in vitro determination of the presence and concentration of ligands in body fluids, food products, animal fluids, and environmental samples. For example, the determination of specific hormones, proteins, therapeutic drugs, and toxic drugs in human blood or urine has significantly improved the medical diagnosis of the human condition. There is a continuing need for simple, rapid assays for the qualitative, semi-quantitative, and quantitative determination of such ligands in a sample. Furthermore, in many situations, such assays need to be simple enough to be performed and interpreted by non-technical users.

Ligand-receptor assays rely on the binding of ligands by receptors to determine the concentration of ligands in a sample. Ligand-receptor assays can be described as either competitive or non-competitive. Non-competitive assays generally utilize receptors in substantial excess over the concentration of ligand to be determined in the assay. Sandwich assays, in which the ligand is detected by binding to two receptors, one receptor labeled to permit detection and a second receptor frequently bound to a solid phase to facilitate separation from unbound reagents, such as unbound labeled first receptor, are examples of non-competitive assays. Competitive assays generally involve ligand from the sample, a ligand analogue labeled to permit detection, and the competition of these species for a limited number of binding sites provided by the ligand receptor. Those skilled in the art will appreciate that many variations of this basic competitive situation have been previously described and will not be discussed in detail herein except where pertinent to the general objectives of this invention. Examples of ligands which are commonly measured by competitive ligand-receptor assays include haptens, hormones and proteins. Antibodies that can bind these classes of ligands are frequently used in these assays as ligand receptors.

Competitive ligand-receptor assays can be further described as being either homogeneous or heterogeneous. In homogeneous assays all of the reactants participating in the competition are mixed together and the quantity of ligand is determined by its effect on the extent of binding between ligand receptor and labeled ligand analogue. The signal observed is modulated by the extent of this binding and can be related to the amount of ligand in the sample. U.S. Pat. No. 3,817,837 describes such a homogeneous, competitive immunoassay in which the labeled ligand analogue is a ligand-enzyme conjugate and the ligand receptor is an antibody capable of binding to either the ligand or the ligand analogue. The binding of the antibody to the ligand-enzyme conjugate decreases the activity of the enzyme relative to the activity observed when the enzyme is in the unbound state. Due to competition between unbound ligand and ligand-enzyme conjugate for antibody binding sites, as the ligand concentration increases the amount of unbound ligand-enzyme conjugate increases and thereby increases the observed signal. The product of the enzyme reaction may then be measured kinetically using a spectrophotometer.

In general, homogeneous assay systems require both an instrument to read the result and calibration of the observed signal by separate tests with samples containing known concentrations of ligand. The development of homogeneous assays has dominated competitive assay research and has resulted in several commercially available systems. Such systems are not, however, capable of providing results for the determination of multiple ligands in a sample in a single-test format not requiring instrumentation.

Heterogeneous, competitive ligand-receptor assays require a separation of bound labeled ligand or receptor from the free labeled ligand or receptor and a measurement of either the bound or the free fraction. Methods for performing such assays are described in U.S. Pat. Nos. 3,654,090, 4,298,685, and 4,506,009. Such methods, however, are not capable of providing semi-quantitative or quantitative results for the determination of ligands in a sample without using additional tests to calibrate the assay response.

The need for ligand-receptor assays that can be performed without the use of instrumentation has led to the development of immunoassays that are simple to perform and result in a response that can be visually interpreted. U.S. Pat. Nos. 4,125,372, 4,200,690, 4,246,339, 4,366,241, 4,446,232, 4,477,576, 4,496,654, 4,632,901, 4,727,019, and 4,740,468 describe devices and methods for ligand-receptor assays that develop colored responses for visual interpretation of the results. While such devices provide simple formats for the visual interpretation of assay results, only the presence or absence of ligand can be determined; semi-quantitative or quantitative determinations using these methods require that separate tests utilizing standards of known concentration be performed to establish the relationship between the observed response and the concentration of ligand.

Methods also have been developed for the internal calibration of ligand-receptor assays by providing devices that incorporate reference zones where the response at the reference zone represents the assay response for a particular concentration of ligand. The response generated by the unknown concentration of ligand in the sample at a test zone is compared with the response at the reference zone to determine the concentration of ligand in the sample either semi-quantitatively or quantitatively. European patent application No. 87302403.8 describes methods for using such internal references in noncompetitive sandwich assays to provide semi-quantitative determinations from visual reading of the results and quantitative determinations from instrumental reading of the results. Likewise, U.S. Pat. No. 4,540,659 and European Patent Application No. 85307785.7 describe systems incorporating references that provide the ability to make semi-quantitative determinations in competitive ligand-receptor assays that are visually interpreted. Both of these systems provide a visual interpretation of the amount of labeled ligand analogue bound to solid phase immobilized receptor.

Employing the techniques described for competitive ligand-receptor assays, the intensity of the resulting color is inversely related to the concentration of ligand in the sample such that assay results that are more intense in color than the reference are interpreted to mean that the sample contained ligand at a lower concentration than that represented by the concentration by the reference. A serious drawback, however, to the widespread utilization of such visually interpreted, competitive ligand-receptor assays has been this inverse relationship between intensity of the developed signal and sample ligand concentration. This relationship provides that a sample with a low concentration of ligand will produce a large signal in the assay; and conversely a sample with a high concentration of ligand will produce a small signal in the assay. A further disadvantage of such assays is that if the requirement is for a single test to simultaneously determine multiple ligands each of which must be assigned a semi-quantitative value and each of which has specific individual concentration targets, then individual specific reference zones would have to be provided for each ligand to be determined. Under such circumstances, a test for multiple ligands becomes difficult to produce and complex to interpret.

Methods have been described in European Patent Applications 87309723.2 and 87309724.0 and in PCT App. No. PCT/US86/00668 (International Publication Number WO 86/06170) where a signal is not developed in the assay until the ligand in the sample exceeds a predetermined amount. These methods utilize ligand receptors immobilized on a solid phase in an array that permits the contact of the ligand in the sample and the ligand analogue conjugate with the immobilized receptors. The contact is made in a chromatographic manner so that the liquid containing the ligand is drawn through the solid phase array in a directional manner. The binding capacity of the solid phase is empirically adjusted so that a predetermined amount of the ligand is bound by the solid phase during the transit of the fluid containing the ligand through the solid phase. The ligand, ligand analogue conjugate, and the array of immobilized receptor do not reach equilibrium during the assay process in these methods. Those skilled in the art will appreciate that the binding capacity of the immobilized receptor is highly dependent upon the immobilization conditions and their affect on the affinity of the receptor for the ligand and on the time during which the ligand and ligand analogue conjugate are able to bind to the immobilized receptor. The reliance of these methods on non-equilibrium conditions causes the manufacture of such assays to be unpredictable and difficult to reproduce. In the present invention equilibrium methods are utilized in order to be able to predict the behavior of assays so that the development of the assay is straightforward and the performance of the assay is reproducible.

The present invention is further directed to simplified methods for the assay of ligands that yield quantitative results. Those skilled in the art will appreciate that quantitative assays require calibration to achieve precise and accurate results. Because competitive assays generally result in non-linear response functions, several calibration points are required for such assays in order to determine the response over the assay range. In order to simplify the calibration process, two extreme approaches have evolved in the prior art. One approach is not to reduce the number of calibrators or replicates needed to determine the response but to reduce the frequency of such calibration. Such assays rely upon instruments to perform the assay and to control variables that affect the assay response so that calibration is infrequent or is performed by the manufacturer and does not need to be performed by the user of the assay. The second approach is to not use an instrument and to provide a simplified means of calibration so that no additional tests are needed to calibrate the assay response. The present invention provides novel methods of calibration which are simple to use in both instrument-based assays and assays that are visually interpreted.

The method of U.S. Pat. No. 4,540,659 provides an assay for the quantitation of ligand in samples where predetermined ratios of responses at a calibration surface and a measurement surface are related to the concentration of the ligand. While this method may provide a crude means of quantitation, it does not offer the precision or the accuracy of existing methods that utilize instruments nor does it provide quantitation without the use of instruments.

Another prior art approach, a non-competitive immunochromatographic assay, is described in U.S. Pat. Nos. 4,168,146 and 4,435,504. This assay provides a method for quantitatively determining the presence of a single analyte in a sample in a visually interpreted immunoassay but does not permit the assay of multiple analytes without employing multiple devices. Furthermore, in practice this method is restricted to ligands whose sample concentrations are high relative to ligands that are commonly determined by competitive assay technology. Accordingly, this type of approach is of limited utility. Clearly, there is an unmet need for a ligand-receptor assay capable of determining the presence of a multiplicity of ligands in a sample and concurrently providing individualized semi-quantitative results for each ligand. Furthermore, such an assay should produce such results in a format that is simple enough for an non-technical user to correctly perform and interpret. In addition there is a need for broadly applicable quantitative assay methods that are easily performed and interpreted. The inventive assays of this invention meet these requirements.

The present invention is a method for performing competitive ligand-receptor assays so as to be able to semi-quantitatively or quantitatively determine the concentration of the ligand. The invention permits the assay of the target ligand to be carried out such that the ligand concentration is determined relative to an internally specified concentration, the threshold concentration. The threshold concentration can be arbitrarily pre-selected to be equivalent to any concentration appropriate to the ligand of interest and serves as a calibration point for the assay of that ligand. The present invention provides quantitative methods that utilize the threshold concentration as a calibration point to enable simplified methods of quantitation. Furthermore, the present invention provides a method for performing competitive ligand-receptor assays for the simultaneous determination of a multiplicity of ligands, each determination including an internal threshold concentration specifically targeted for its respective ligand. One embodiment of the present invention is a method for performing competitive ligand-receptor assays for the simultaneous determination of a multiplicity of ligands, each determination including a compendium of internal threshold concentrations specifically targeted for the respective ligand. The method of the present invention affords the concentration determination to be carried out in a manner which is simple to employ and straightforward to interpret.

SUMMARY OF THE INVENTION

The present invention is directed to a ligand receptor assay having three major elements and an additional optional element:

1) A reaction phase and mixture;
2) An optional means for removing selected species from the reaction mixture;
3) A terminal solid phase; and
4) A signal development phase.

The reaction phase comprises, in part, receptor for target ligand and ligand analogue conjugate. Ligand analogue conjugate comprises ligand analogue or ligand analogues bound to a signal development element. The ligand analogue portion of the ligand analogue conjugate is capable of competing with target ligand for the limited number of binding sites present on ligand receptor. A reaction mixture is formed from the sample and the reaction phase which includes ligand analogue conjugate and ligand receptor. The amounts of ligand receptor and ligand analogue conjugate are selected such that when the reaction mixture substantially approaches equilibrium binding conditions, substantially all of the ligand analogue conjugate is bound ligand receptor when ligand is present at less than the threshold concentration. Subsequently, the reaction mixture is contacted with the next element of the ligand-receptor assay.

At this point, the reaction mixture can be contacted either with an optional means for removing ligand receptor from the reaction mixture, or can be immediately contacted with the terminal solid phase. Whether or not an optional means is necessary or desirable depends on a variety of factors, including the analytes of interest, their concentrations and the chosen assay format. The optional means can be used effectively, for example, in the assay of ligands in which the concentration range to be spanned is so large that a "hook" effect is possible. This disclosure describes specific assay formats employing an optional means. Other applications will be apparent to those skilled in the art. As used herein, the term "optional means" refers to a device or substance which may be operatively associated with (i.e., may complex to) a receptor directed against ligand receptor, i.e., a (ligand receptor) receptor. Thus, when the reaction mixture contacts the optional means, the (ligand receptor) receptor binds with all species associated with ligand receptor. In the reaction mixture this includes ligand receptor, ligand:ligand receptor complex and ligand analogue conjugate:ligand receptor complex. Alternatively, the optional means can be part of the reaction phase, or it can be introduced into the reaction mixture during the approach to equilibrium.

The reaction mixture is next contacted with the terminal solid phase. The terminal solid phase has non-diffusively immobilized ligand receptor capable of binding available ligand or ligand analogue conjugate. A portion of the ligand and ligand analogue conjugate not bound to ligand receptor in the reaction mixture then binds to the terminal solid phase immobilized ligand receptor. If necessary, the remainder of the reaction mixture may then be removed using a washing step. The washing step removes any ligand analogue conjugate which has not bound to ligand receptor immobilized on the terminal solid phase; thus, only ligand analogue conjugate bound to the terminal solid phase is left remaining.

The terminal solid phase which now contains ligand analogue conjugate:ligand receptor complex then is contacted with a signal development phase. The signal development phase enables the signal development element of the ligand analogue conjugate bound to the solid phase to produce a detectable signal. Interpretation of the detectable signal is such that the absence of a detectable signal indicates either that the target ligand is not present in the sample or that the target ligand is present in the sample at a concentration less than the threshold concentration. A detectable signal on the other hand, is indicative of the presence of the target ligand either at a concentration substantially equivalent to, or at a concentration greater than the threshold concentration. Simple calibration methods are enabled by the present invention so that the ligand concentration can be quantitatively determined.

Definitions

In interpreting the claims and specification, the following terms shall have the meanings set forth below.

Ligand—Binding partner to ligand receptor.

Ligand Analogue—A chemical derivative of the target ligand which may be attached either covalently or non-covalently to other species for example to the signal development element. Ligand analogue and ligand may be the same and both are capable of binding to ligand receptor.

Ligand Receptor—Receptor capable of binding ligand, typically an antibody, but which may be a ligand.

Ligand Analogue Conjugate—A conjugate of a ligand analogue and a signal development element.

Signal Development Element—The element of the ligand analogue conjugate which, in conjunction with the signal development phase, develops the detectable signal, e.g., an enzyme.

Threshold Concentration—The concentration of ligand in a sample which results in the first detectable signal development. A threshold concentration is a concentration reference point.

Reaction Phase—The phase normally containing the ligand analogue conjugate, e.g., hapten-enzyme conjugate, and ligand receptor, e.g., an antibody.

Reaction Mixture—The mixture of sample suspected of containing the target analyte and the reaction phase.

Ligand:Ligand Receptor Complex—The complex which occurs when ligand is bound by ligand receptor.

Ligand Analogue Conjugate:Ligand Receptor Complex—The complex which occurs when ligand analogue conjugate is bound by ligand receptor.

Optional Means—An optional means which is operatively associated with a receptor, e.g., an antibody which is capable of binding with selected components of the reaction mixture.

Terminal Solid Phase—The solid phase upon which the signal is finally developed during the signal development step.

Signal Development Phase—The phase containing the materials enabling the signal development element to develop signal, e.g., an enzyme substrate solution.

Ligand Complement—A specialized ligand used in labeling ligand analogue conjugates, receptors, ligand analogue constructs or signal development elements.

Ligand Complement Receptor—A receptor for ligand complement.

Ligand Analogue—Ligand Complement Conjugate—A conjugate composed of a ligand analogue, a ligand complement and a signal development element.

Reference Ligand—A ligand complement used to produce a reference ligand conjugate for use in providing a reference concentration point.

Reference Receptor—A receptor capable of binding with a reference ligand.

Reference Ligand Conjugate—A conjugate consisting of a reference ligand and a signal development element.

Reference Concentration—A reference concentration is developed using a reference ligand conjugate and a reference receptor. It is used in conjunction with the threshold concentration to define a range of concentrations.

Negative Control Ligand—A ligand complement used to produce a negative control ligand conjugate. A negative control ligand and (negative control ligand) receptor afford a means to ensure the validity of an assay result.

(Negative Control Ligand) Receptor—A receptor capable of binding with a negative control ligand.

Ligand Receptor Conjugate—A conjugate of a ligand receptor and a signal development element.

Ligand Analogue Construct—A ligand analogue linked to a solid phase or to another molecule such that when bound to ligand receptor conjugate, ligand receptor conjugate is prevented from binding to immobilized ligand analogue on the terminal solid phase.

DETAILED DESCRIPTION OF THE INVENTION

Figure 1:
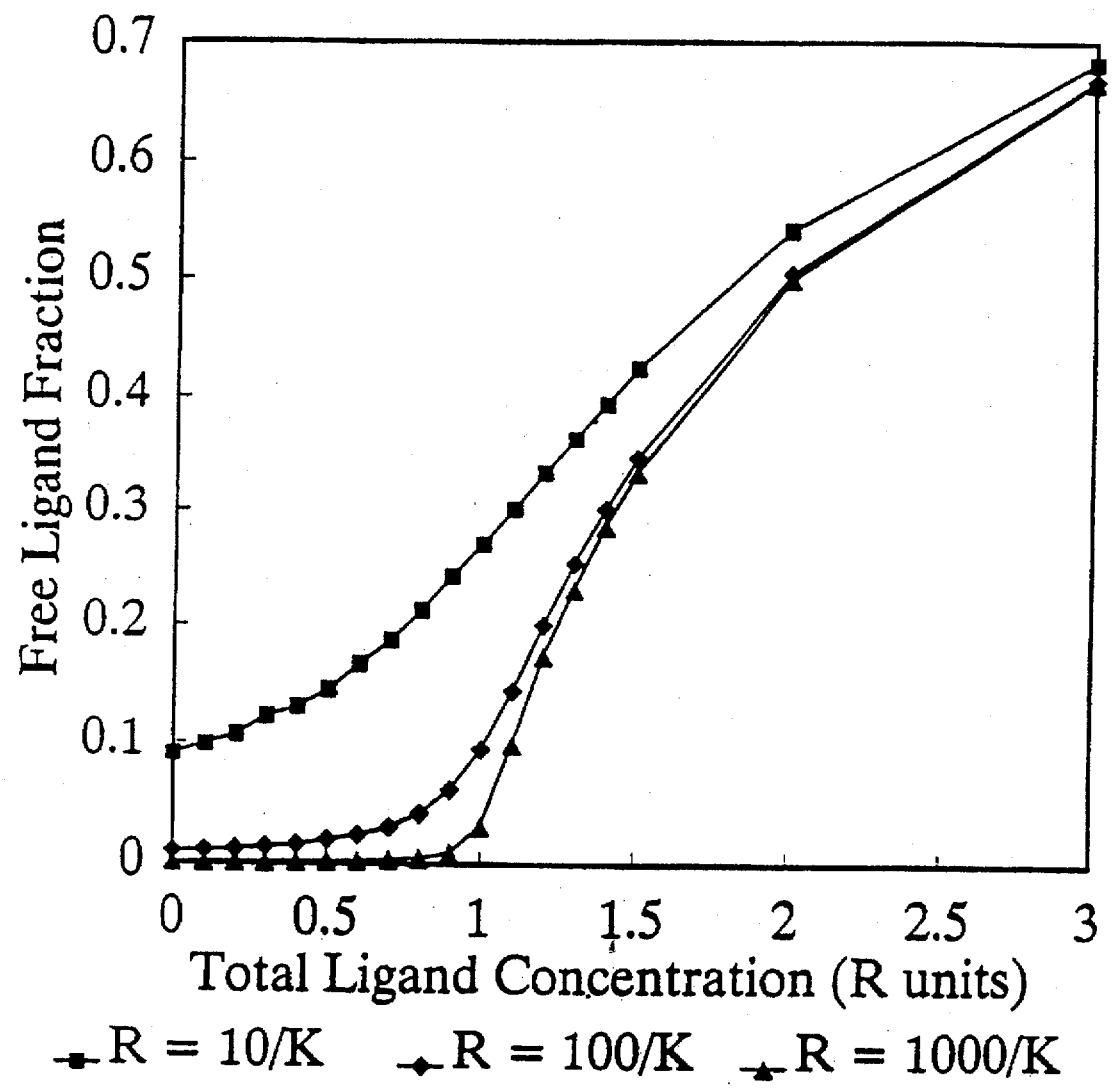
FIG. 1 is a graph showing the fraction of total unbound ligand as a function of total ligand. The graph shows that as the value of K increases relative to that of L and R the functional form of a plot of free ligand as a function of total ligand concentration approaches a step function.

The aforementioned four elements of the ligand-receptor assays of the present invention, namely 1) a reaction phase and mixture; 2) an optional means for removing selected species from the reaction mixture; 3) a terminal solid phase; and 4) a signal development phase will be explained in detail in this section.

Reaction Phase and Mixture

The reaction phase normally contains both a ligand analogue conjugate comprised of a conjugate of a ligand analogue and a signal development element, and a ligand receptor. A preferred embodiment of the present invention employs ligand receptor in the reaction phase immobilized on a non-diffusive solid phase. In a particularly preferred embodiment of the present invention the ligand receptor is not immobilized on a non-diffusive solid phase and is thereby free to diffuse in solution.

Generally, methods for preparing the first reaction phase reagents of the present invention entail consideration of the following factors. Coupling of the ligand analogue to the signal development element to produce a ligand analogue conjugate must be accomplished such that recognition of the coupled ligand analogue by the ligand receptor directed against the uncoupled ligand is not substantially compromised. The number of ligands coupled to a signal development element must be sufficient to ensure that the ability of ligand analogue conjugate to compete with ligand for binding sites on the ligand receptor is not substantially compromised. Similarly, the number of ligand analogues coupled to a signal development element must not be so great as to substantially compromise the ability of ligand to compete with ligand analogue conjugate for binding sites on the ligand receptor. Preferred for the present invention are ligand analogue conjugates in which the number of ligand analogues coupled to the signal development element are between 1 and 50. Particularly preferred for the present invention are ligand analogue conjugates in which the number of ligand analogues conjugated to the signal development element are between 1 and 10.

A signal development element is an element which can produce a detectable signal. Those skilled in the art will recognize that many elements are capable of functioning as a signal development element, including without limitation, radionuclides, fluorescent species, phosphorescent species, chemiluminescent materials, dyes, enzymes, and sol particles that may incorporate metals, semi-metals, non-metals or any of the above species. A preferred signal development element for the present invention is one which produces a signal capable of being detected by non-instrumental means. A particularly preferred signal development element is one which produces a signal capable of being detected by visual means, for example, an enzyme capable of reacting with an enzyme substrate in which the product of the enzymatic reaction is a molecule which absorbs electromagnetic radiation in the visible region of the electromagnetic spectrum. A particularly preferred signal development element is colloidal gold, a sol particle that is colored. Methods for the adsorption of proteins to colloidal gold are described in Georghegan, et al., *J. Histochem. Cystochem.*, 25, 1187–1200 (1977) and in Leuvering, U.S. Pat. No. 4,313,734. Proteins with coupled ligand analogues may be similarly adsorbed to colloidal gold to provide a ligand analogue conjugate that is useful in assays that are visually interpreted. Particularly preferred for the present invention are colloidal gold particles that are 10–80 nanometers in diameter and where the number of ligand analogues coupled to each particle is between 10 and 10,000.

Selection of ligand receptors to provide the complementary reagent for the ligand analogue conjugate must be accomplished with an understanding of the factors which control response function curves in competitive saturation ligand receptor assays. Some of these factors are discussed in R. P. Ekins, G. B. Newman and J. L. H. O'Riordan, *Theoretical Aspects of "Saturation" and Radioimmunoassay*, Radioisotopes in Medicine: In Vitro Studies, R. L. Hayes, F. A. Goswitz and B. E. P. Murphy, Eds. U.S. Atomic Energy Commission Oak Ridge, Tenn., 59–100 (1968), incorporated by reference herein. (All of the references hereinafter herein cited are hereby incorporated by reference.) Of particular importance among such factors are the equilibrium binding constant of the ligand receptor for ligand and the width of the function describing the distribution of equilibrium binding constants for such an ensemble of ligand receptors. Preferred for use as ligand receptors in immunoassays are antibodies, particularly preferred antibodies for use as ligand receptors are monoclonal antibodies. Methods for generation of monoclonal antibodies are well known to those skilled in the art. Monoclonal antibodies can be readily developed with binding constants greater than $10^8 M^{-1}$ and due to monoclonality, antibody ensembles derived from a single cell line and directed against a specific ligand can be produced with a narrow distribution of equilibrium binding constants.

Ekins, et al. have shown that the general form of the reaction which describes binding of a ligand by a ligand receptor selected from an ensemble of such ligand receptors may be represented by the expression $$L+R_i=LR_i$$

where L represents the ligand and $R_i$ represents the binding site of the ith ligand receptor species with i=1,2,3, ... n. The expression describing equilibrium binding is given as $$K_i[L][R_i]=[LR_i]$$

where $K_i$ is the equilibrium binding constant describing the reaction in which $R_i$ binds L. For the simplest case in which all $R_i$ have equal equilibrium binding constants, a closed solution for the expression can be obtained to relate the fraction of unbound ligand to the total amount of ligand for a fixed amount of receptor. This situation is of particular interest when the equilibrium binding constants, K, for binding of ligand to ligand receptor and for binding of ligand analogue conjugate to ligand receptor are substantially equivalent. The closed form solution for the simplest case in which all $R_i$ are equal is given by Ekins as $$(F_{fb})^2+F_{fb}(1-\underline{L}/\underline{R}-1/K\underline{R})-1/K\underline{R}=0$$

where $F_{fb}$ is the ratio of free to bound ligand, is the total concentration of ligand, $\underline{R}$ is the total concentration of ligand receptor binding sites and K is the equilibrium binding constant. Accordingly, the present invention shows that as the value of $\underline{R}$ increases relative to that of 1/K the functional form of a plot of free ligand as a function of total ligand concentration approaches that of a step function as illustrated in FIG. 1. The present invention further shows that the curvature at the step is related to the relationship between the equilibrium binding constant, K, and the total ligand receptor binding site concentration, $\underline{R}$. In FIG. 1 the function plotted is the fraction of total ligand which is free (unbound) as a function of total ligand. As $\underline{R}$ increases relative to 1/K, it can be seen from FIG. 1 that a more dramatic step increase in free ligand fraction occurs. In the usual case, one selects ligand receptors of increasing equilibrium constant, K, to achieve a dramatic stepwise increase in the free ligand fraction. The relationship between free ligand fraction and the ratio of free to bound ligand, $f_{fb}$, is given below $$\underline{L}_f/\underline{L}=F_{fb}/(F_{fb}+1).$$

Figure 2:
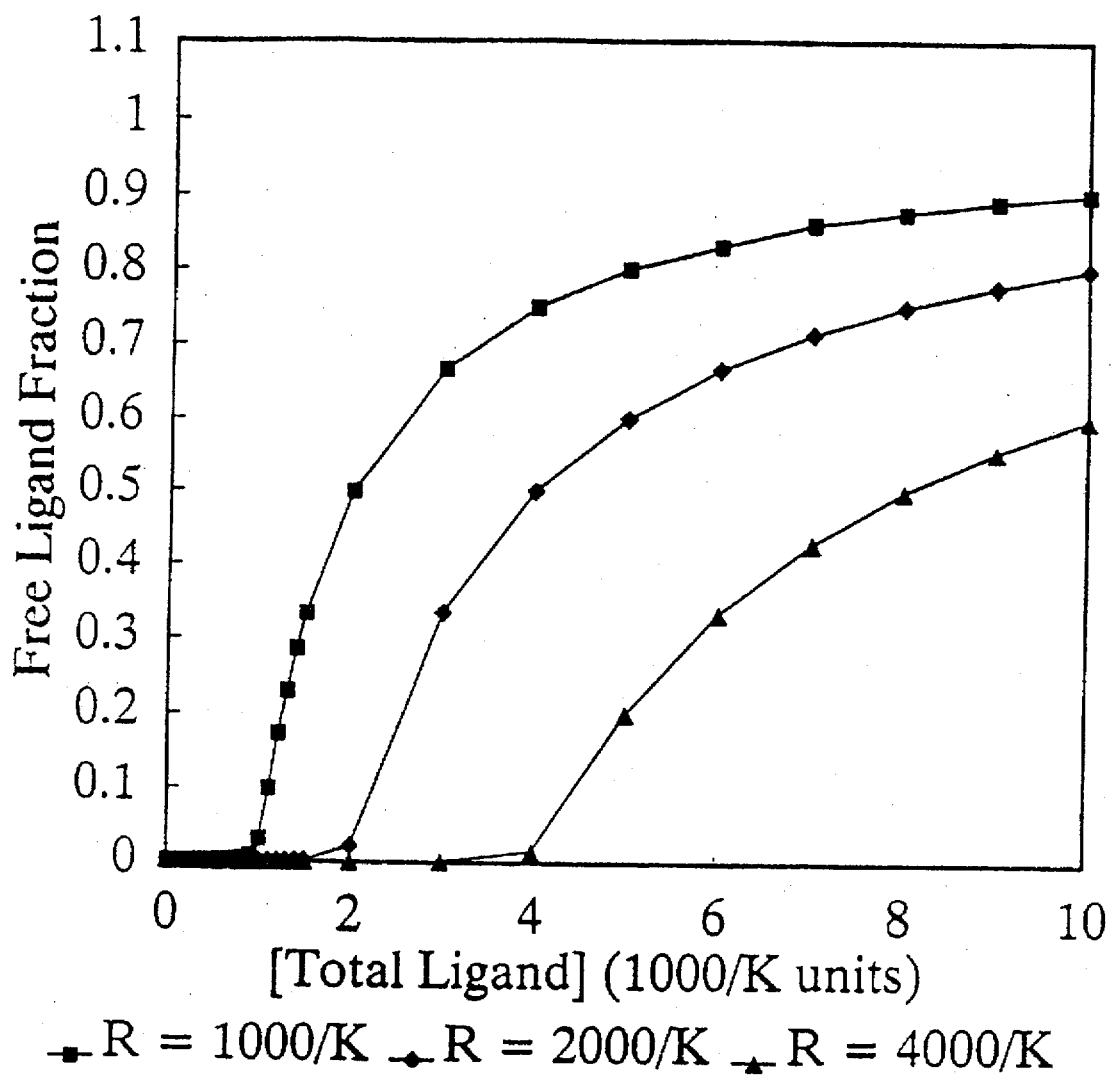
FIG. 2 is a graph showing the effect of the variation in ligand receptor concentration. The graph shows that increasing the value of R increases the ligand concentration corresponding to the positzon of the step.

The present invention makes use of these relationships and further extends this concept by showing that when $\underline{R}$ is sufficiently larger than 1/K, then the concentration position of the step is a function of the relative values of R. As is illustrated in FIG. 2, increasing the value of $\underline{R}$ increases the concentration corresponding to the position of the step.

In order to make use of these relationships in ligand receptor as says, ligand analogue conjugate and ligand receptor must be provided such that when contacted with sample in a reaction mixture, and after equilibrium binding has been substantially achieved, in the absence of ligand in the sample, substantially all of the ligand analogue conjugate is bound by ligand receptor. Those skilled in the art will appreciate that the amount of ligand receptor can be selected so that binding sites in excess of the number required to bind substantially all of the ligand analogue conjugate are provided in the reaction mixture. When the amount of ligand in the sample exceeds the amount of excess binding sites, then ligand and ligand analogue conjugate start to compete for available ligand receptor binding sites. The concentration of ligand in the sample that results in the first detectable increase in the amount of unbound ligand analogue conjugate in the reaction mixture at substantially equilibrium binding is the threshold concentration. As illustrated in FIG. 2, the threshold concentration can be selected by appropriate choice of the concentration of ligand receptor in the reaction mixture. The application of this method to visual assays is of particular importance because the visible product of the assay response can be easily controlled so that no response is observed until the ligand exceeds its threshold concentration. As demonstrated by FIG. 1, the rate of increase of the unbound ligand analogue conjugate and the fraction of unbound ligand analogue conjugate when ligand is present at less than the threshold concentration are determined by the equilibrium binding constant and its relationship to the threshold concentration. The equilibrium binding constant should be sufficient to reduce the response due to the unbound ligand analogue conjugate to below the response noise of the assay provided by other sources of noise. Those skilled in the art will understand that the ligand analogue conjugate, the signal development phase, and the assay process in combination determine the response noise of the assay. Preferred for use as ligand receptors in the present invention are ligand receptors of equilibrium binding constant greater than $10^2 \times$(threshold concentration)$^{-1}$ particularly preferred for use are ligand receptors of binding constant greater than $10^3 \times$(threshold concentration)$^{-1}$.

The assay response described by the present invention was not achieved by the prior art. The prior art teaches that the free fraction of ligand analogue conjugate in the absence of ligand should be a significant fraction of the total ligand analogue conjugate in the assay in order to maximize sensitivity. In the present invention, substantially all of the ligand analogue conjugate is bound either in the absence of ligand or when the ligand concentration is less than the threshold concentration.

Figure 3:
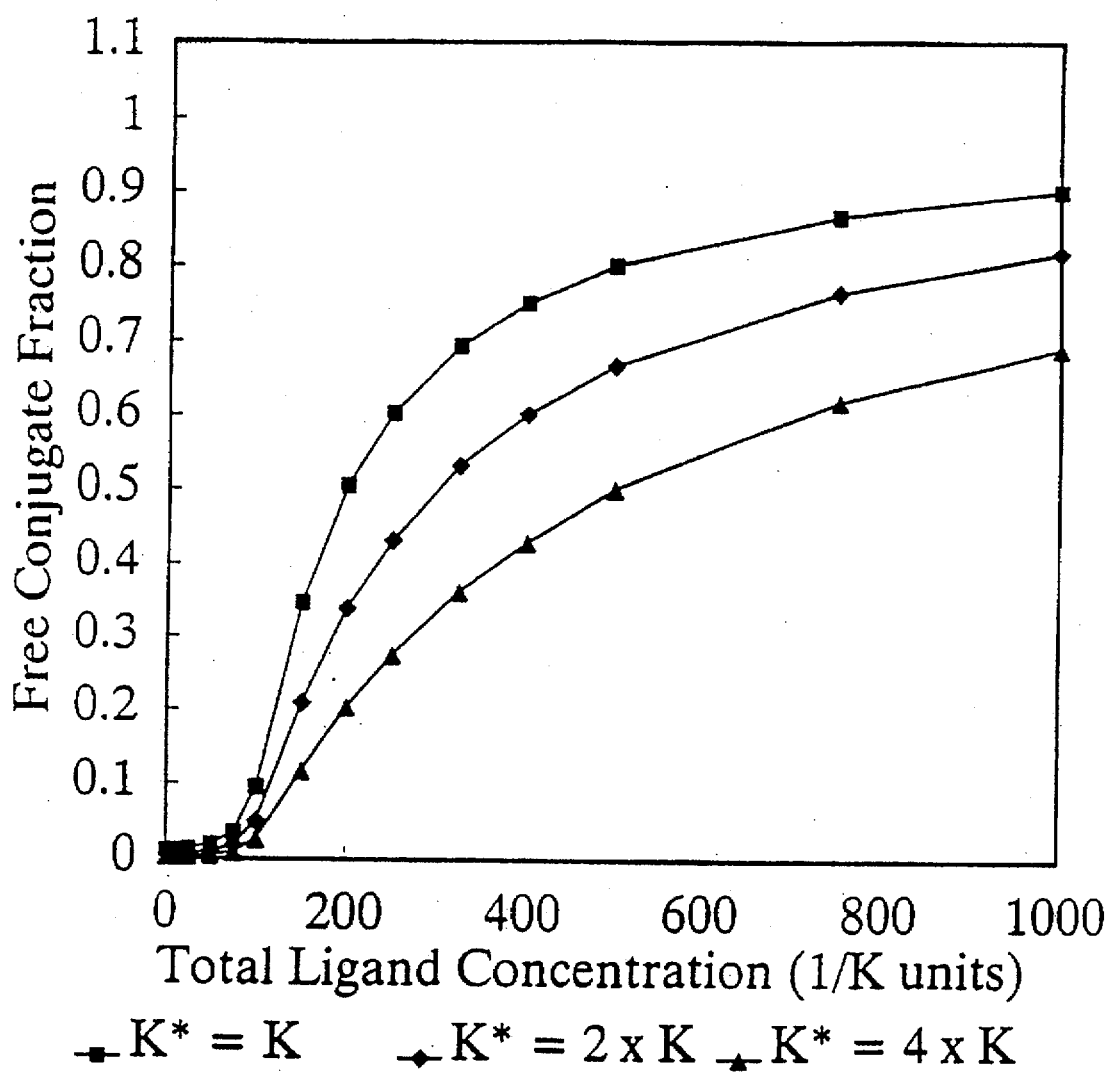
FIG. 3 is a graph showing the response function for ligand-receptor assays in which the equilibrium binding constants are not substantially equivalent for the binding of ligand to ligand receptor and for the binding of ligand analogue conjugate to ligand receptor. The concentration of receptor binding sites is 0.1 in units of 1/K.

The present invention is further directed to examples of ligand-receptor assays in which the equilibrium binding constants are not substantially equivalent for the binding of ligand to ligand receptor and for the binding of ligand analogue conjugate to ligand receptor. In particular, the present invention shows that the slope of the response function above the threshold concentration is determined by the magnitude of the equilibrium binding constant of the ligand receptor for the ligand analogue conjugate relative to the magnitude of the equilibrium binding constant of the ligand receptor for the ligand. When these binding constants are substantially equivalent, the response functions depicted in FIG. 1 describe the assay response. When the binding constants are not substantially equivalent, the response function varies as depicted in FIG. 3. When the magnitude of the equilibrium binding constant of the ligand receptor for the ligand analogue conjugate (K*) is greater than the magnitude of the equilibrium binding constant of the ligand receptor for the ligand, the slope of the response function is reduced since more ligand is required to compete effectively with a given concentration of ligand analogue conjugate. Similarly, when the magnitude of the equilibrium binding constant of the ligand receptor for binding to ligand analogue conjugate is less than the magnitude of the equilibrium binding constant for binding to ligand the slope of the response function is correspondingly increased because less ligand is necessary to compete with a given concentration of ligand analogue conjugate.

Therefore, the slope of the response function can be varied by varying the magnitude of the equilibrium binding constant of the ligand receptor for ligand analogue conjugate. This variation is most readily achieved in practice by varying the number of ligand analogues per signal development element. Conjugates with higher ratios of ligand analogue to signal development element exhibit larger magnitude equilibrium binding constants for binding with the ligand receptor and have response functions that have correspondingly reduced slopes relative to conjugates less derivatized with ligand. Ligand analogues can be coupled by different means to signal development elements to change their equilibrium binding constants for ligand receptor. Thereby, one can design ligand analogues that exhibit larger or smaller magnitude equilibrium binding constants than does the ligand for the ligand receptor. The ability to empirically adjust the slope of the response function is beneficial in optimizing assays.

For example, in the present invention, the preferred method for performing threshold immunoassays (as described herein) utilizes soluble antibody and a ligand analogue conjugate in a reaction phase to which is added a sample potentially containing target ligand. This mixture is allowed to come substantially to conditions of equilibrium binding. In the absence of target ligand, substantially all of the ligand analogue conjugate is bound to antibody and is not available for binding to antibody immobilized on the terminal solid phase.

The reaction phase can be provided in many ways. The correct relative and absolute amounts of ligand analogue conjugate and antibody must be provided in order to pre-establish a threshold concentration of target ligand below which little or no signal is developed. One method is to mix a fixed sample volume with a fixed amount of ligand analogue conjugate, add this mixture to a fixed amount of antibody, and allow the final mixture to come substantially to conditions of equilibrium binding. A second method is to add a fixed sample volume to a fixed antibody volume and then add a fixed amount of ligand analogue conjugate. A third method is to add sample to a mixture of ligand analogue conjugate and antibody. If antibody and ligand analogue conjugate have been allowed to react prior to the addition of ligand from the sample, the dissociation of the ligand analogue conjugate:antibody complex becomes the rate limiting step governing the approach to conditions of equilibrium binding. For large ligand analogue conjugates this can prove to be an unacceptably long period of time for most applications.

One practical consideration is the expense of the antibody and ligand analogue conjugate reagents. For ligands in which the threshold concentration is desired to be 1 µM or greater, the cost of the reagents may become significant and therefore, the reagent volumes should be small to produce a cost effective assay kit. In order to address this consideration, a preferred method for providing the antibody and ligand analogue conjugate reagents is to co-lyophilize them without permitting them to react with one another. Such a process can be accomplished by adding the correct volume of the first reagent to a vial and freezing it, followed by the addition of the correct volume of the second reagent to the vial with rapid freezing to avoid melting of the first reagent and thereby possible mixing of the two reagents. The two frozen reagents are then co-lyophilized. Alternatively, the antibody and ligand analogue conjugate reagents may be separately lyophilized in bulk and mixed together as dry formulations in the appropriate amounts.

Accordingly, the present invention affords a ligand receptor assay process which includes a step function-like element in the assay response function curve and concurrently provides a mechanism for associating the position of the step with a specific selected ligand concentration, the threshold concentration, which is selectable by adjustment of the relative values of the concentrations of the ligand analogue conjugate and the ligand receptor.

Figure 4:
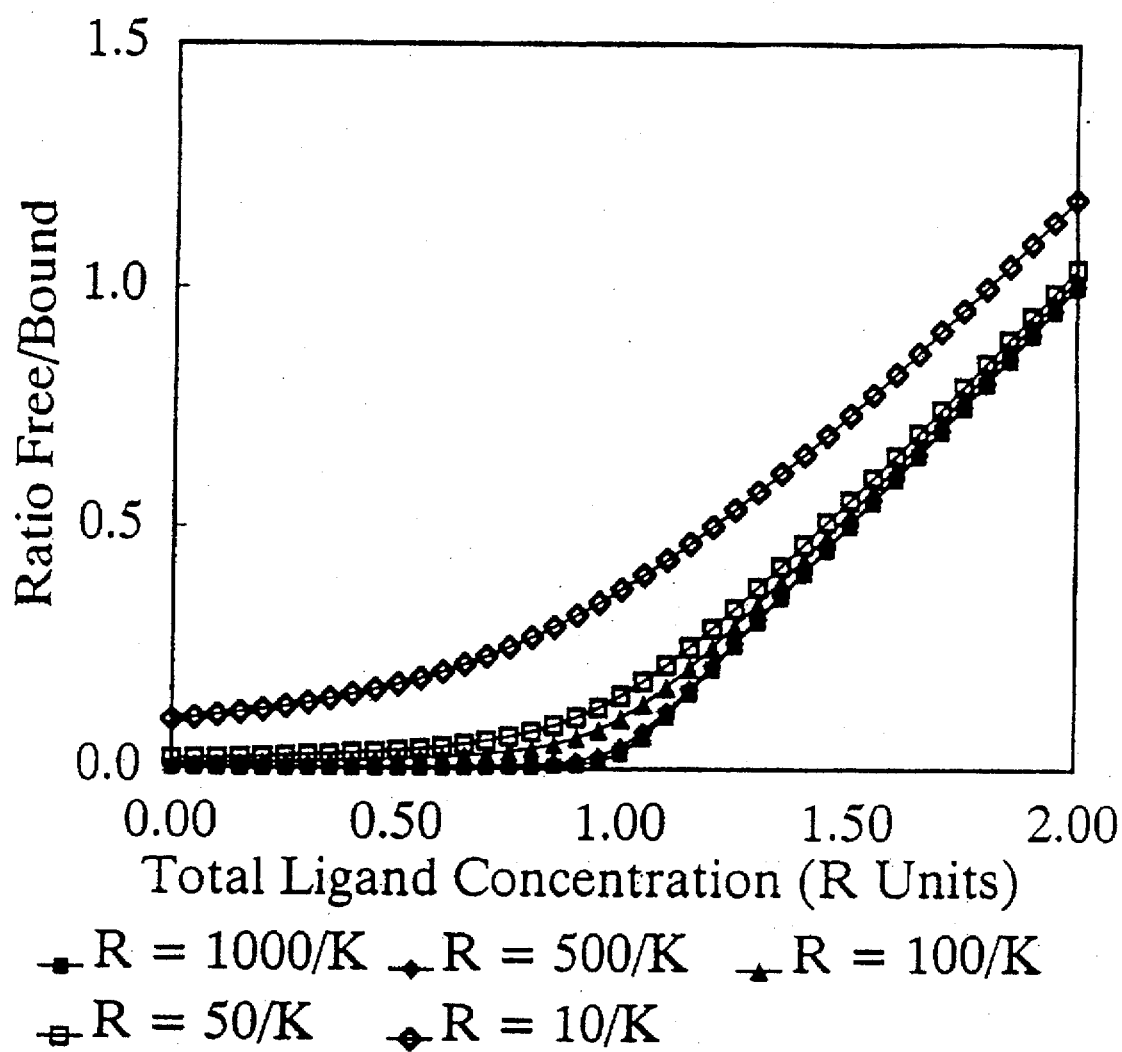
FIG. 4 is a graph showing the response functions for ligand-receptor assays plotted as a function of the ratio of the free to the bound ligand analogue conjugate fraction versus ligand concentration. The graph shows that as the value of R increases relative to the value of 1/K, the ratio of the free to the bound conjugate fraction approaches a linear function of the ligand concentration above the threshold concentration.
Figure 5:
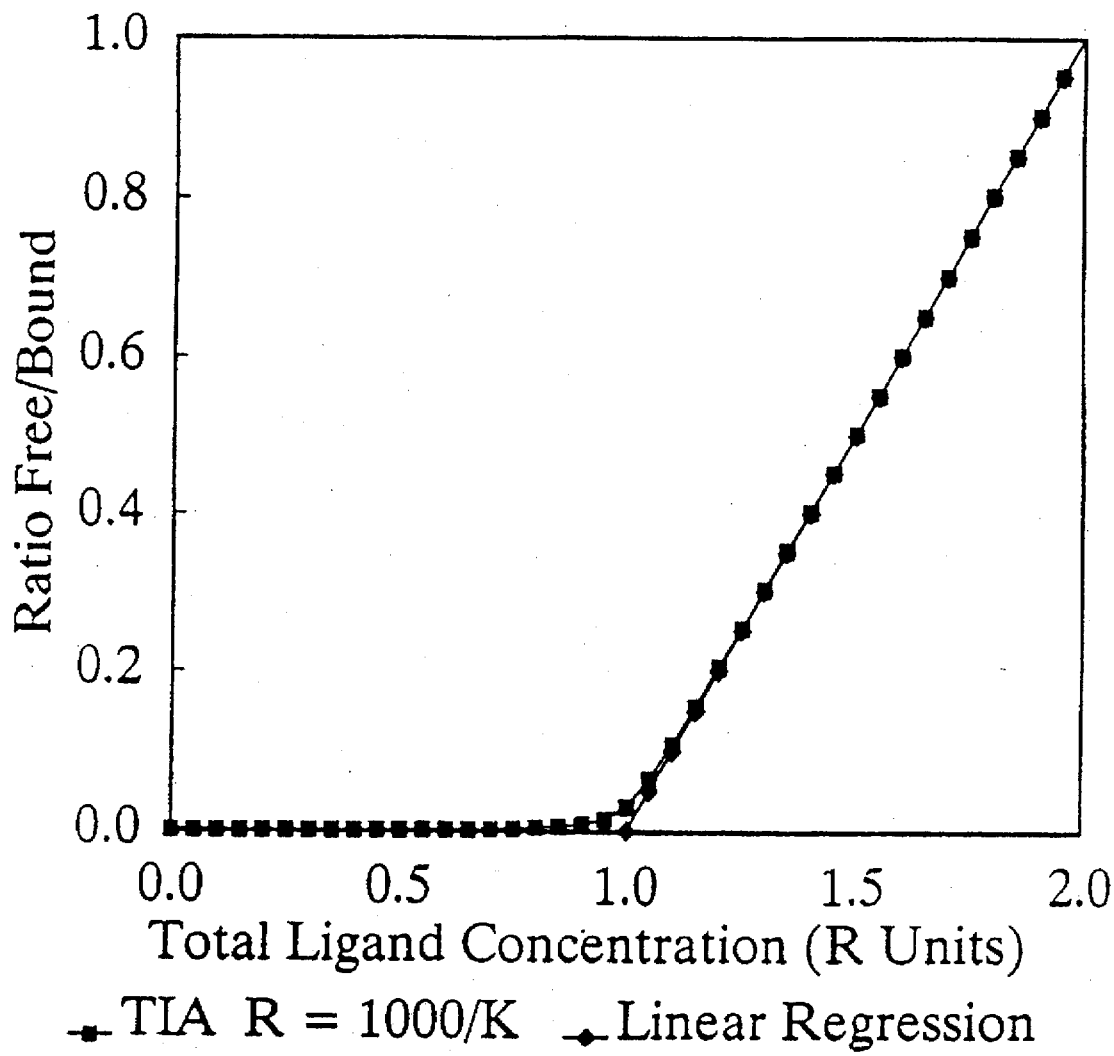
FIG. 5 is a graph showing the response function for ligand-receptor assay plotted as a function of the ratio of the free to the bound ligand fraction versus ligand concentration compared to a theoretically derived straight line function. The graph shows that the linear approximation agrees very well with the assay response under these conditions.
Figure 6:
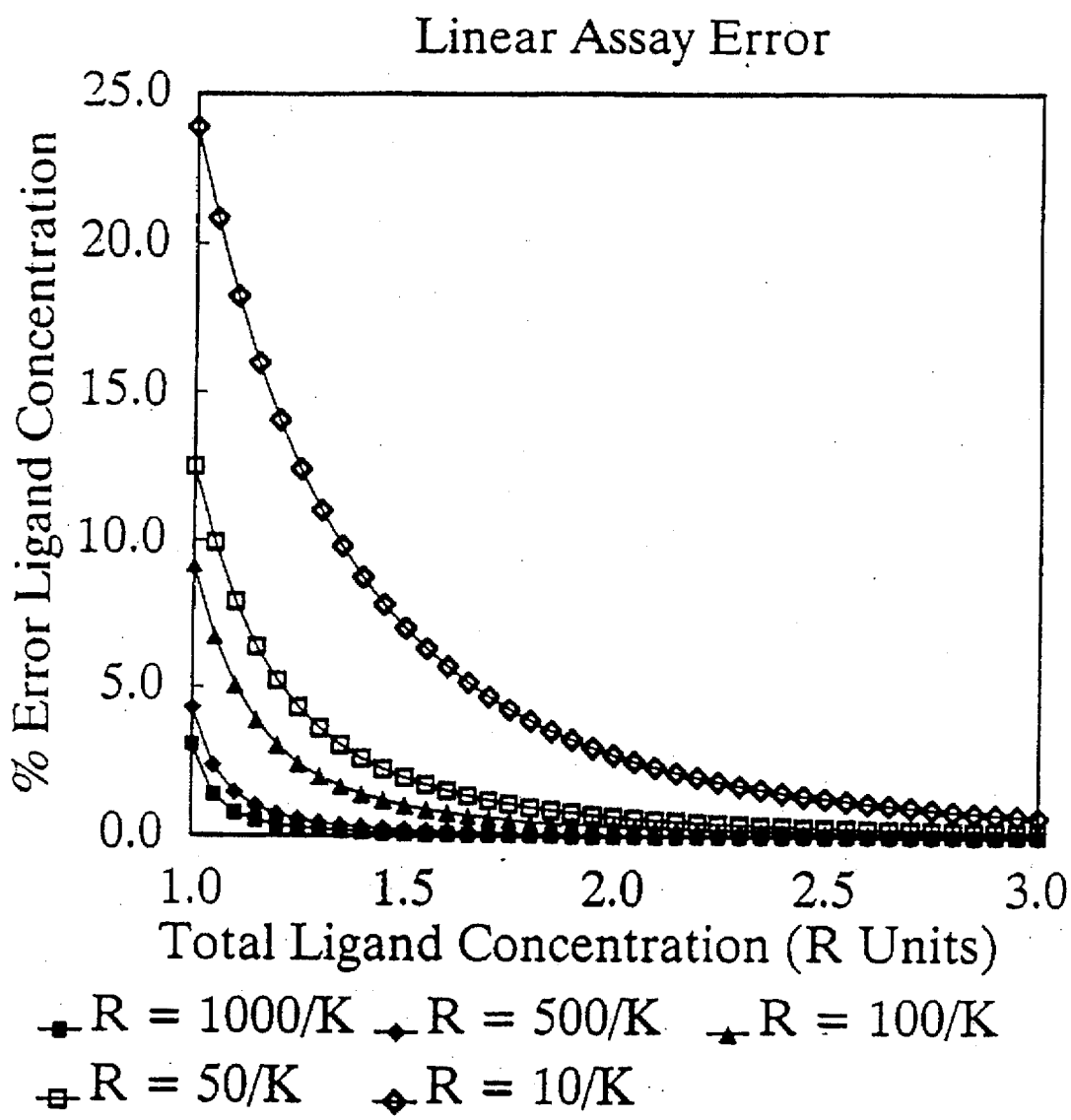
FIG. 6 is a graph showing the difference of the theoretically derived concentration function derived from the ratio of free to bound ligand fractions response curve and a theoretical linear concentration function as a function of ligand concentration. The graph shows that the error introduced by the linear approximation can be made negligibly small over substantially the entire assay range.

The present invention is further directed to simplified methods for quantitative assays. Ekins, et al. show that the ratio of free to bound ligand is a hyperbolic function of the ligand concentration and that as the ratio of free to bound ligand becomes large, it asymptotically approaches a linear function. In constructing assays it is the ligand analogue conjugate that is actually measured as a reflection of the state of the ligand. When an assay is constructed using the principles of the present invention, the ratio of free to bound ligand analogue conjugate is a linear function of the ligand concentration over substantially the entire assay range. The slope of the line and its intercepts of the axes are constant parameters of the assay system for a given set of reagents. FIG. 4 depicts theoretical plots of the ratio of free to bound ligand analogue conjugate as functions of the total ligand concentration where the affinity of the receptor for the ligand is greater than the inverse of the receptor concentration. If the affinities of the receptor for the ligand and for the ligand analogue conjugate are equal, then these plots are the same for the ligand and the ligand analogue conjugate. As described by FIG. 3, the affinity of the receptor for the ligand analogue conjugate relative to the affinity of the receptor for the ligand affects the slope of the assay response. This is true for the response when it is expressed as the ratio of free to bound ligand analogue conjugate also. For the examples described here, the affinities of the receptor for the ligand and for the ligand analogue conjugate are equal. As the ratio of the affinity for the ligand analogue conjugate to the inverse of the receptor concentration approaches 1000, the ratio of free to bound ligand analogue conjugate approaches a linear function of the ligand concentration over the entire assay range. When the ratio of free to bound ligand analogue conjugate is plotted as a function of the ligand concentration, plots like those of FIG. 4 are obtained. In FIG. 5 the plot of the theoretical ratio of free to bound ligand analogue conjugate and a linear regression obtained from the same theoretical data using only high ratios are compared. When the affinity of the receptor for the ligand analogue conjugate is approximately 1000× larger than the inverse of the receptor concentration as shown in FIG. 5, then the ratio of free to bound ligand analogue conjugate is a linear function of the ligand concentration over substantially the entire assay range. The error introduced in determining the concentration of the ligand by using the linear approximation of this invention can be estimated by taking the difference in ligand concentration predicted from the theoretical response and determined by the linear approximation and expressing the error as a percentage of the ligand concentration as shown in FIG. 6. When the affinity of the receptor for the ligand analogue conjugate is sufficiently high, the error in the ligand concentration as estimated from the linear approximation becomes insignificantly small relative to the typical errors introduced by other aspects of the assay.

The slope and the intercept of the linear function can be determined for a given set of reagents by performing the assay with calibrators that lie in the range of ligand concentrations where the function is strictly linear. Because the slope and the intercept are constant parameters of the assay system, their values only need to be determined once, for example by the manufacturer. In order to determine the assay response as a function of the ligand concentration, the ratio of free to bound ligand analogue conjugate must be related to the assay response. This can be achieved with a single calibration point. Those skilled in the art will appreciate that signal development elements can be used such that the assay response is directly proportional to the free ligand analogue conjugate concentration. The ratio of free to bound ligand analogue conjugate for the calibrator is then given by $$\text{ratio} = \frac{(\text{calibrator response})}{(\text{maximum response}) - (\text{calibrator response})}$$

where the maximum response is the assay response when all of the ligand analogue conjugate is free. Because the ratio of free to bound ligand analogue conjugate for the calibrator is a known constant, the calibrator response defines the maximum response according to the above equation. This maximum response is then used to calculate the ratio of free to bound ligand analogue conjugate for the unknown response given by $$\text{ratio} = \frac{(\text{unknown response})}{(\text{maximum response}) - (\text{unknown response})}$$

This ratio and the linear function determine the unknown concentration of the ligand in the sample. Thus, a single calibrator can be used to assay samples quantitatively if a competitive assay is performed using the principles taught by this invention.

Optional Means for Removal of Ligand Receptor From Reaction Mixture

An optional means for removing ligand receptors from the reaction mixture may be included whenever it is necessary or desirable to prevent ligand analogue conjugate: ligand receptor complexes in the reaction mixture from contacting the terminal solid phase. Such an optional means is necessary if, for example, ligand analogue conjugate:ligand receptor complex in the reaction mixture dissociates to a significant extent during incubation with the terminal solid phase such that terminal solid phase immobilized ligand receptor could bind dissociated ligand analogue conjugate and result in a detectable signal even in the absence of target ligand. The optional means for removing ligand receptors from the reaction mixture may be any device means for binding ligand receptors so that they are removed from the reaction mixture prior to contacting the reaction mixture with the terminal solid phase. For example, such an optional means may consist of (ligand receptor) receptors and solid phase supports for immobilization of these (ligand receptor) receptors, such that through binding of reaction mixture ligand receptors to (ligand receptor) receptors immobilized on the solid phase support of the optional means, the ligand receptors and ligand receptor associated complexes are prevented from contacting ligand receptors bound to the terminal solid phase. Examples of receptors and solid phases which may be useful in constructing optional means for the removal of ligand receptors include anti-antibody antibodies such as goat-anti-mouse IgG or goat-anti-mouse Fc, receptors such as protein A and protein G, and solid phases such as diffusible beads, macroporous agarose beads, membranes, filters, and porous matrices. Alternatively, ligand complement receptors immobilized on solid phases may be used to remove ligand receptors labeled with ligand complement from the reaction mixture, e.g., ligand receptors labeled with biotin can be bound by avidin immobilized on solid phases. Ligand receptors also can be precipitated from the reaction mixture using a (ligand receptor) receptor. When beads are used as the solid phase, receptors for ligand receptors are normally immobilized on the beads and the beads may be added to the reaction mixture as part of the reaction phase, during the incubation of the reaction mixture, or after the reaction mixture has substantially achieved equilibrium binding. Centrifugation or filtration may be necessary to remove the beads from the reaction mixture prior to contact with the terminal solid phase. When porous matrices, including membranes and filters, are used as the solid phase, the reaction mixture can be contained within the porous matrix or the reaction mixture can be introduced to the porous matrix after conditions of equilibrium binding have been substantially approached. In either case the porous matrix functions to remove ligand receptors and their complexes prior to contact with the terminal solid phase.

Terminal Solid Phase

The terminal solid phase is a solid support having localized ligand receptors for target ligands and ligand analogue conjugates. The terminal solid phase of the invention may be a solid support onto which are localized ligand receptors in distinct loci capable of binding both target ligands and ligand analogue conjugates. In the context of the present invention, the term "localized" encompasses all physical mechanisms for immobilizing receptors such that during the performance of the ligand-receptor assay process substantially all of the receptor remains in a predetermined locus. Such mechanisms include covalent binding, noncovalent binding, chemical coupling, physical entrapment of particulates operatively associated with receptors, and adsorption by hydrophobic/hydrophobic or hydrophilic/hydrophilic interactions. The localization of the ligand receptor onto the solid support of the solid phase of the present invention may be accomplished in a number of ways. The ligand receptor may be localized by the technique of entrapping ligand receptor coated particulates by a porous matrix solid support. Methods for introducing said particulates to a porous matrix are discussed in U.S. Pat. Nos. 4,446,232, 4,740,468 and European Patent Application 86302521.9, incorporated by reference herein. A particularly preferred method of localization of the ligand receptor onto the solid support wherein the solid support is a porous matrix comprises in part, localization of the ligand receptor on the solid support by covalent or non-covalent chemical binding. Techniques for binding ligand receptors to a solid support are well known in the art. A variety of solid supports, including a porous matrix, a non-porous matrix, beads, membranes or filters, may be used in the present invention. Such solid supports can be incorporated into a variety of test devices including dipsticks and devices such as those described in U.S. Pat. Nos. 4,200,690, 4,246,339, 4,366,241, 4,632,901, and 4,727,019. A particularly preferred solid phase is a membrane suspended in a device such that when the reaction mixture is contacted with the membrane, the reaction mixture is of sufficient volume to completely fill the void volume of the exposed membrane such that the total surface area of the membrane and all receptor zones are contacted by the reaction mixture. Such a device would also incorporate, if necessary, a means for removal of unbound conjugates from the membrane and a means for contacting the signal development phase with conjugates bound to immobilized receptors on the membrane.

Clearly the use of the method of the present invention with such devices would provide one with the ability to assay for multiple analytes in a single sample using a single test device which will provide threshold immunoassay results for each analyte. In the multiple simultaneous ligand assay formats a solid support comprising for each ligand to be determined, at least one discrete reaction zone on which is localized one said ligand receptor may be used. Furthermore, the incorporation of internal negative controls, positive references, and calibrators in discrete reaction zones will add to the information provided by the assay result.

Furthermore, the preferred terminal solid phase as described above is particularly useful where it is highly desirable to simultaneously determine the presence of more than one ligand of interest, such as for the determination of causative agents of a toxicological response. This may be readily accomplished by binding of ligand receptors within discrete zones of the support matrix. Such a solid phase system provides, in essence, a panel of ligand receptors capable of screening for toxins which may be present in a patient fluid sample. Accordingly the pattern of reactivity on the solid phase system, as determined by the presence of bound toxin analogue conjugates, provides an indication of the nature of the toxins eliciting the toxicological response.

Therefore, in one of the embodiments of the present invention, the reaction mixture which may contain in part, ligand, ligand analogue conjugate, ligand receptor, ligand:ligand receptor complex and ligand analogue conjugate-:ligand receptor complex is contacted with a terminal solid phase upon which is immobilized ligand receptor. In a preferred embodiment the terminal solid phase is composed of a non-diffusible bead, membrane or filter upon which the receptor is immobilized. In a particularly preferred embodiment, the terminal solid phase is composed of a porous matrix upon which the ligand receptor is immobilized. The ligand receptor can be immobilized by a variety of methods including but not limited to direct covalent chemical attachment, indirect covalent chemical attachment, direct non-covalent chemical attachment, indirect non-covalent chemical attachment and physical entrapment. In a preferred embodiment the ligand receptor immobilized on the terminal solid phase is capable of binding with ligand analogue conjugate. Furthermore, in a preferred embodiment for application of the present invention to immunoassays the ligand receptor is an antibody. In a particularly preferred embodiment the ligand receptor immobilized on the terminal solid phase is identical to the ligand receptor which is included in the reaction phase mentioned above which first contacts the sample. In another particularly preferred embodiment for application of the present invention to immunoassays, the ligand receptor is a monoclonal antibody.

Signal Development Phase

The signal development phase is a phase which enables the signal development element to produce a detectable signal. Elements of the signal development phase may exist in any or all of the following assay components, the reaction phase, the optional means, the terminal solid phase, and the signal development phase. Preferred for use as components of the signal development phase are materials which enable the signal development phase to produce a signal which is detectable by non-instrumental means. Particularly preferred for use as components in the signal development phase are materials which enable the signal development element to produce a signal detect- able by visual means. Those skilled in the art will appreciate that a variety of materials can be used to accomplish this end, by way of example the following is offered; an enzyme substrate solution, e.g., 3-indoxyl phosphate, which when contacted with the terminal solid phase containing bound enzyme is converted by the enzyme, e.g., calf intestinal alkaline phosphatase (E.C. 3.1.3.1), to a visible, blue-.colored reaction product, indigo. Another example of a signal development phase comprises channeling methods as described in U.S. Pat. No. 4,233,402 when used in conjunction with a terminal solid phase as described in U.S. Pat. No. 4,391,904. Such methods substantially eliminate the need to remove unbound conjugates by a washing mechanism; they are preferred as the signal development phase of this invention. When sol particles such as colloidal gold are used as the signal development element, a simple washing of the terminal solid phase is generally sufficient to reveal the assay signal so that a signal development phase is unnecessary.

Ligand-Receptor Assay Process

To begin the ligand-receptor assays of the present invention one introduces a fluid sample suspected of containing a target ligand to the reaction phase of ligand analogue conjugate and ligand receptor. Competition occurs between the ligand analogue conjugate and the target ligand for the limited number of binding sites available on the ligand receptor. The relative amounts of ligand analogue conjugate and ligand receptor are such that in the absence of target ligand, and subsequent to the achievement of substantially equilibrium binding, substantially all of the available ligand analogues on the ligand analogue conjugate are bound. One skilled in the art will appreciate that for fixed amounts of ligand analogue conjugate and ligand receptor that the volume of the sample can be varied to vary the threshold concentration. Significant amounts of unbound ligand analogue conjugate are not present unless the sum of the effective concentration of ligand analogue on the ligand analogue conjugate and the, concentration of target ligand begins to exceed the concentration of available ligand receptor binding sites. As used herein, the term "unbound" means a conjugate having at least one available ligand analogue capable of binding to ligand receptor. The ligand anaogue conjugate may have more than one ligand analogue and may have ligand receptor bound to it, nevertheless, as long as it has at least one additional available ligand analogue capable of binding to ligand receptor it may be termed "unbound". "Bound" ligand analogue conjugates are those which do not have any ligand analogues available for binding. It should be understood that the effective concentration of ligand analogue conjugate is dependent on the number of antibody binding sites that can be bound to a single conjugate molecule. Therefore, heavily derivatized conjugates containing many ligand analogues will have higher ligand analogue concentrations than less derivatized conjugates. The concentration of ligand which results in the first significant increase in unbound ligand analogue conjugate resulting in an assay response detectable above the background noise is the threshold concentration. Those skilled in the art will appreciate that the background noise of the assay is dependent upon the assay process and the nature of the ligand analogue conjugate and the signal development phase. It is generally desirable for the background noise to be less than 1% of the maximum response. As the amount of ligand increases above the threshold concentration, the amount of ligand analogue conjugate not bound to ligand receptor also increases. The increase in the amount of unbound ligand analogue on the ligand analogue conjugate continues until the amount of target ligand has increased to such a value that substantially all of the ligand analogue conjugate exists in a state in which it is unbound to ligand receptor.

In a preferred embodiment of the present invention the ligand receptor in the reaction phase is not non-diffusively immobilized and is therefore capable of diffusive motion during the competition reaction for ligand receptor binding sites which occurs between ligand and ligand analogue conjugate. In a particularly preferred embodiment, the target ligand and the ligand analogue conjugate participate in a competition for binding sites on the diffusible ligand receptor. In a particularly preferred embodiment, the present invention provides a process for an immunoassay in which the ligand receptor is a monoclonal antibody free to diffuse in solution. The reaction mixture contains in part, ligand, ligand analogue conjugate, ligand receptor, ligand:ligand receptor complex and ligand analogue conjugate:ligand receptor complex. Subsequent to the competition reaction the reaction mixture is then contacted with an optional means operatively associated with a (ligand receptor) receptor. The optional means associated (ligand receptor) receptor binds to all species associated with ligand receptor. Accordingly, the optional means associated (ligand receptor) receptor can bind to ligand receptor, ligand:ligand receptor complex and ligand analogue conjugate:ligand receptor complex from the reaction mixture. Removal of ligand receptor associated components from the reaction mixture by the optional means allows only the unbound ligand analogue conjugate to be contacted by the terminal solid phase immobilized ligand receptor. Thus, when an optional means is used to remove ligand receptor and moieties bound to ligand receptor from the reaction mixture, the unbound ligand analogue conjugate in the reaction mixture refers to ligand analogue conjugate that is not bound to ligand receptor. If only one ligand is being determined by an assay process that uses an optional means to remove receptor from the reaction mixture, then the signal due to the free ligand analogue conjugate in the reaction mixture can be determined directly without the need for a terminal solid phase.

The reaction mixture is then contacted with the terminal solid phase upon which is immobilized ligand receptor. Accordingly, the present invention provides a process where the ligand receptor is immobilized on a solid phase. Preferred solid phases for use in immobilizing the receptor include diffusible beads, membranes and filters. Particularly preferred for use as the solid phase for immobilization of the receptor is a porous matrix. The ligand receptor immobilized on the terminal solid phase contacts the components of the reaction mixture, which consist in part of, unbound ligand, and unbound ligand analogue conjugate. If the reaction mixture has not been contacted with an optional means the reaction mixture also may contain uncomplexed ligand receptor, ligand:ligand receptor complex and ligand analogue conjugate:ligand receptor complex. When the reaction mixture has not been contacted with an optional means, unbound ligand analogue conjugate refers to ligand analogue conjugates that are capable of binding to immobilized ligand receptors on the terminal solid phase even though ligand receptors from the reaction mixture already may be bound to some ligand analogues on the ligand analogue conjugate. A competition occurs between any unbound ligand and any unbound ligand analogue conjugate for available binding sites on the ligand receptor immobilized on the terminal solid phase. After allowing binding reactions to proceed, the terminal solid phase and the reaction mixture may be separated. Any ligand analogue conjugate which has not bound to the ligand receptor immobilized on the terminal solid phase is removed if necessary, by a separation step. The ligand analogue conjugate complexed with the ligand receptor immobilized on the terminal solid phase is contacted with a signal development phase which enables the signal development element of the complexed ligand analogue conjugate to develop a detectable signal. Interpretation of the signal is such that absence of a signal detectable above the assay background noise indicates that the target ligand is at a concentration in the sample lower than the threshold concentration, while presence of a signal detectable above the assay background noise indicates that the target ligand is either at a concentration substantially equivalent to or at a concentration greater than the threshold concentration.

Negative Control Ligand

The reaction mixture of the present invention should be allowed to come substantially to equilibrium prior to contact with the terminal solid phase so that in the presence of target ligand at less than the threshold concentration, the ligand analogue conjugate is bound substantially completely by ligand receptor in the reaction mixture and cannot bind to immobilized ligand receptor on the terminal solid phase. In order to determine that the reaction mixture has properly approached equilibrium and subsequent assay results are valid, a preferred method for practicing this invention is the inclusion of a negative control ligand conjugate. The negative control ligand is a ligand not normally found in samples. The combination of negative control ligand conjugate, ligand analogue conjugate, ligand receptor and (negative control ligand) receptor is provided such that when the assay is performed properly, no response is observed at the (negative control ligand) receptor locus on the terminal solid phase because the reaction mixture has substantially achieved equilibrium binding conditions where substantially all of the negative control ligand conjugate is bound by (negative control ligand) receptors in the reaction mixture. If insufficient time is allowed for the reaction mixture to substantially approach equilibrium or if the signal development phase is incorrectly performed, responses may be observed at the ligand specific test loci that falsely indicate the presence of target ligands at greater than the threshold concentrations. Under these circumstances, the negative control locus would also exhibit an observable response and would indicate that the test is invalid. Such a negative control provides assurance that the assay protocol has been performed correctly and confirms the validity of any positive results. Those skilled in the art will appreciate that the relative and absolute concentrations of the negative control ligand conjugate and the negative control ligand receptor can be adjusted to control the incubation time required to substantially reach equilibrium binding conditions. The time to equilibrium can be adjusted to equal the time required to achieve equilibrium for the slowest ligand-receptor pair in the assay. Ligands which are useful as negative control ligands may be selected from the same general class of ligands not normally present in samples of interest (i.e., ligand complements) but which can be used to generate ligand complement conjugates and ligand complement receptors which exhibit the appropriate affinity for the ligand. Such ligands include, for example, fluorescein.

In order to ensure that all reaction zones on the terminal solid phase have been contacted by the reaction mixture, a preferred method for the practice of this invention is the inclusion of a positive control ligand conjugate in the reaction mixture. A positive control ligand receptor is immobilized in a discrete zone on the terminal solid phase so that when the reaction mixture is contacted with the terminal solid phase, the positive control ligand conjugate binds to its respective receptor and a detectable signal results at the positive control zone on the terminal solid phase. The position and shape of the positive control zone on the terminal solid phase can be selected such that all of the other discrete receptor zones on the terminal solid phase must be contacted with the reaction mixture if the positive control zone is contacted with the reaction mixture. For example, if the reaction mixture is contacted with a terminal solid phase at one end of a rectangular strip, the positive control zone can be placed at the other end of the strip with all of the discrete reaction zones lying between the two ends of the strip. A detectable result in the positive control zone further signifies that the signal development element and the signal development phase are functioning properly to generate assay responses if free conjugates in the reaction mixture bind to the solid phase. Ligands that are useful as the positive control ligand may be selected from the same class of ligands (i.e., ligand complements) as negative control ligands.

A negative control ligand conjugate, a negative control ligand receptor, a positive control ligand conjugate, and a positive control ligand receptor can be used to determine that the relative and absolute amounts of the ligand analogue conjugates and the ligand analogue receptors in the reaction mixture were not supplied grossly in error. Generally, all ligand analogue conjugates, including negative and positive control ligand conjugates are supplied as a mixture. Similarly, all of the ligand analogue receptors, including the negative and positive control ligand receptors, are supplied as a mixture. The relative and absolute amounts of each ligand analogue conjugate and ligand analogue receptor pair are selected to provide a threshold concentration for the determination of each ligand in the assay. If an error in the filling of the reagents occurs as an isolated incident that does not affect a substantial portion of a manufacturing lot, the error may not be detected by statistical quality control testing procedures but would result in an assay that could generate a false positive or a false negative result. Normally, such problems can only be uncovered by testing 100% of the manufactured product by destructive means. This is a clearly unacceptable solution to the problem. The present invention utilizes positive and negative controls so that in every assay, the correct reagent formulation is either confirmed and the assay is validated or it is shown to be in error and the assay is invalidated. To achieve these objectives, the negative control ligand conjugate can be adjusted such that the negative control ligand receptor is in slight excess, for example 10%, over the amount needed to bind all of the negative control ligand conjugate. Similarly, the positive control ligand conjugate and the positive control ligand receptor are provided such that the positive control ligand conjugate is in slight excess, for example 10%, over the amount that can be bound by the positive ligand receptor. If the negative control ligand conjugate is mistakenly provided in excess by greater than 10% of its targeted amount, then all of the other ligand analogue conjugates would be in similar excess, and the resulting response in the negative control zone on the terminal solid phase would signal the error and invalidate the result. Similarly, if the positive control ligand receptor is mistakenly provided in excess by greater than 10% of its targeted amount, then all of the other ligand receptors would be in similar excess, and the resulting lack of a response in the positive control zone on the terminal solid phase would signal the error and invalidate the result. Such control mechanisms provide a means to test each assay for the proper reagent formulation.

Use of Threshold Concentration and Reference Point to Determine Concentration Range of Ligand A preferred method of this invention utilizes a threshold concentration to define the lower limit of a concentration range for a target ligand and a reference point to determine the upper limit of that concentration range. The reference response is at a locus distinct from the locus of the test response and is further chosen to represent the response produced by a target ligand concentration corresponding to the upper limit of the concentration range. The response at the reference locus can be provided by a ligand-receptor pair in which the reference receptor is immobilized at the reference locus and the reference ligand is labeled with a signal development element to permit detection, for example, using a reference ligand conjugate. Ligands which are useful for such purposes are ligands that are not normally found in samples of interest, i.e., ligand complements, so that no competition occurs between reference ligand conjugate and target ligand for either reference receptor or ligand receptor binding sites. Ligands such as fluorescein are useful as reference ligands for this purpose and fluorescein-labeled enzymes are useful as reference ligand conjugates in conjunction with anti-fluorescein antibodies as reference receptors for the purpose of providing a reference response to determine whether the assay response at the test locus corresponds to a ligand concentration that is less than or substantially equivalent to or greater than the upper limit of the concentration range. Alternatively, the signal development element itself could function as the reference ligand conjugate, e.g., enzyme could be used with an anti-enzyme antibody as the reference receptor. Since the slope of an assay response function can be selected by adjusting the degree of derivatization of the ligand analogue conjugate, the assay response function can be optimized in order to extend the full dynamic range of the assay response function over the selected range of target ligand concentrations. This approach affords the maximum ability to assess whether the concentration of target ligand is above, below, or within the selected concentration range. No signal development in the test locus indicates that the sample contains target ligand at less than the lower limit of the concentration range. Detectable signal development which is less than the reference response indicates that the sample contains target ligand at a concentration within the selected concentration range. Assay responses substantially equivalent to or greater than the reference response indicate that the sample contains target ligand concentrations above the selected concentration range. The use of references that represent predetermined concen- trations of ligands in competitive assays have been described in U.S. Pat. No. 4,540,659 and European Patent Application 85307785.7. However, these applications would require two such reference points to determine a concentration range. By necessity, these methods compress the dynamic range of assay response which one could use for the range of selected ligand concentrations. For this reason, the method of the present invention for utilizing such references is a significant improvement for performing such competitive ligand-receptor assays in which the concentration of the ligand is determined relative to two predetermined ligand concentrations. The method of the present invention is of particular utility in determining ligand concentration relative to a selected concentration range.

Ligand-Receptor Assay Process for the Quantitative Determination of Ligands Using a Single Calibration Point A preferred method of this invention utilizes a single calibration point to quantitatively assay a target ligand over a range of concentration. The single calibration point can be provided either as an external calibrator response from a separate test performed at the same time as the test of the sample or as a reference response at a locus distinct from the locus of the test response. The external calibrator response or the reference response is further chosen to represent the response produced by a specific target ligand concentration with a ratio of free to bound ligand analogue conjugate that is a constant for a given set of assay reagents. The maximum response of the assay is determined by the calibrator or referenceresponse according to the relationship $$\text{ratio} = \frac{(\text{calibrator response})}{(\text{maximum response}) - (\text{calibrator response})}$$

The maximum response is used to determine the ratio of free to bound ligand analogue conjugate from the assay response for the unknown ligand concentration in the sample using the relationship $$\text{ratio} = \frac{(\text{unknown response})}{(\text{maximum response}) - (\text{unknown response})}$$

The ratio of free to bound ligand analogue conjugate corresponding to the unknown ligand concentration, together with the known slope and intercept of the ratio of free to bound ligand analogue conjugate as a function of the ligand concentration, determine the unknown ligand concentration in the sample.

In order to use the responses described above to determine the ratios of free to bound ligand analogue conjugate, the assay response must be directly proportional to the concentration of free ligand analogue conjugate in the reaction mixture when the binding reactions have reached substantially equilibrium conditions. If the free ligand analogue conjugate in the reaction mixture is sampled directly, for example, by using an optional means to remove the bound ligand analogue conjugate and then measuring the remaining free ligand analogue conjugate, the only further requirement is that the signal development element together with the signal development phase result in a response that is proportional to the concentration of the free ligand analogue conjugate that is sampled. The choice of an enzyme as the signal development element and a substrate solution that generates product in direct proportion to the amount of enzyme present as the signal development phase are preferred for signal generation in the present invention. Particularly preferred is the use of colloidal gold as the signal development element for which no signal development phase is necessary. If the free ligand analogue conjugate is sampled by contacting the reaction mixture with a terminal solid phase, then the ligand receptor immobilized on the solid phase must bind an amount of ligand analogue conjugate that is directly proportional to the amount of free ligand analogue conjugate that is present in the reaction mixture. In addition the signal development element together with the signal development phase must provide a signal that is directly proportional to the amount of the ligand analogue conjugate that is bound to the terminal solid phase. When the single calibration point is provided by an external calibrator run as a separate test, a calibration sample containing a known concentration of the target ligand is provided in addition to the slope and intercept of the ratio of free to bound ligand analogue conjugate as a function of the ligand concentration. When the single calibration point is provided by a reference response on a terminal solid phase, the response at the reference locus can be provided by the mechanisms previously discussed for the reference point. The response must represent the test response obtained for a known concentration of ligand and must have a known ratio of free to bound ligand analogue conjugate associated with it so that a maximum assay response is determined. The test response on the terminal solid phase must be proportional to the concentration of free ligand analogue conjugate in the reaction mixture as described above. Those skilled in the art will appreciate that the ligand receptor immobilized on the terminal solid phase at the test zone must be in excess over the combination of ligand and ligand analogue conjugate contacted with the test zone so that the amount of ligand analogue conjugate bound to the test zone is directly proportional to the concentration of the free ligand analogue conjugate in the reaction mixture. These processes provide simplified methods for the quantitation of ligands in samples that do not require extensive external calibration to define the assay response or expensive instrumentation to control the variables that affect assay response so that less frequent calibration is necessary.

Visual Ligand Receptor Assay Process for the Quantitative Termination of Ligands The linear relationship between the ratio of free ligand to bound ligand in the reaction mixture provides the basis for a visual, quantitative assay. At concentrations of ligand above the threshold concentration, the concentration of bound ligand is substantially constant so that the concentration of free ligand is substantially a linear function of the ligand concentration above the threshold concentration. In a reaction mixture, if the concentration of the ligand in the sample is above the threshold concentration, then the sum of the concentrations of the free ligand and the free ligand analogue conjugate is a linear function of the ligand concentration. When such a reaction mixture is contacted with an immunochromagraphic device such as described in U.S. Pat. No. 4,435,504, the free ligand and the free ligand analogue conjugate bind to immobilized receptors on the terminal solid phase. The migration distance over which the ligand analogue conjugate is bound to the solid phase is directly proportional to the concentration of ligand in the sample if the receptor is capable of binding both the ligand and the ligand analogue conjugate. Unless the concentration of the ligand is above the threshold concentration, the migration distance of ligand analogue conjugate bound to the terminal solid phase is zero. Thus, the concentration of ligand that first develops a visual response can be selected to be the threshold concentration and the migration distance of the colored response is directly proportional to the concentration of ligand in the sample exceeding the threshold concentration so that calibration of the assay is achieved without the need for external calibrators or instruments. The assay permits the quantitation of ligand in samples at concentrations where the concentration of ligand analogue conjugate is larger than the clinically significant concentration of ligand in the sample and therefore avoids the limitations of the prior art.

Ligand Receptor Assay Process for a Ligand Utilizing Ligand Analogue-Ligand Complement Conjugate In another embodiment of the ligand-receptor assays of this invention, the ligand analogue conjugate is augmented by the inclusion of a specialized ligand, termed a ligand complement. The ligand complement is a ligand not normally found in samples to be tested. The inclusion of a ligand complement creates a conjugate with both ligand analogue and ligand complement bound to the signal development element. A fluid sample is contacted with a reaction phase having a complementary reaction pair of ligand analogue-ligand complement conjugate and ligand receptor for the target ligand of interest. The ligand receptor may be an antibody immobilized on a solid phase. The target ligand and the ligand analogue-ligand complement conjugate compete for binding sites on the solid phase immobilized ligand receptor. If the target ligand is present at less than the threshold concentration, substantially all of the ligand analogue-ligand complement conjugate is bound to ligand receptor. In a particularly preferred embodiment the ligand receptor is a monoclonal antibody free to diffuse through the reaction mixture. When the ligand receptor is free to diffuse in the reaction mixture, an optional means for removing ligand receptors from the reaction mixture is needed prior to contacting the terminal solid phase containing immobilized ligand complement receptor. The inclusion of a ligand complement in the ligand analogue conjugate eliminates the potential "hook" effect problem.

In certain assay formats, a hook effect may occur when the remaining amount of unbound ligand which contacts the terminal solid phase is so large that it efficiently competes with unbound ligand analogue conjugate for binding sites on the immobilized ligand receptor. When the competition greatly favors binding of target ligand, then the signal developed by any ligand analogue conjugate: ligand receptor complexes formed on the terminal solid phase may be so small as to be undetectable. The assay would then be incorrectly interpreted as indicating that the concentration of the target ligand in the sample was below the threshold concentration. In the present invention, using a terminal solid phase containing an immobilized receptor which is directed against a complement ligand (i.e., a ligand complement receptor) can overcome this limitation. When the reaction mixture is placed in contact with a terminal solid phase having an immobilized ligand complement receptor, no competition occurs between remaining target ligand and ligand analogue-ligand complement conjugate for binding sites on the immobilized ligand complement receptor. Under these circumstances binding of ligand analogue-ligand complement conjugate will be both maximal and unaffected by residual target ligand. A hook effect will not occur and the target ligand concentration may be correctly interpreted. Therefore, following contact of the terminal solid phase with a signal development phase, absence of a detectable signal indicates the ligand to be at a concentration less than the threshold concentration, while presence of a detectable signal indicates the presence of ligand at a concentration substantially equivalent to or greater than the threshold concentration.

Ligand-Receptor Assay Process for the Simultaneous Determination of Multiple Ligands The present invention is particularly useful in the performance of simultaneous multiple ligand-receptor assays. Any number of non-interacting complementary ligand analogue conjugate:ligand receptor reaction pairs can be employed concurrently to determine multiple target ligands of interest in a single sample.

In the assays of the present invention, a fluid sample suspected of containing target ligands of interest is contacted with a reaction phase containing complimentary ligand analogue conjugate::ligand receptor reaction pairs in a number equal to the number of target ligands to be determined. A competition occurs between target ligands and their respective ligand analogue conjugates for binding sites on the complementary ligand receptor. The multiple non-interacting competitive reactions all are allowed to approach substantially equilibrium binding conditions. At equilibrium for each of the competitive systems the amount of unbound ligand analogue conjugate will be determined by a number of factors, of particular importance being the amount of the respective target ligand present in the sample. In the absence of the specific target ligand, essentially all of the respective ligand analogue conjugate will be bound by the appropriate ligand receptor. At equilibrium, detectable amounts of the specific ligand analogue conjugate will only be present when the target ligand concentration is substantially equivalent to or greater than the respective threshold concentration. To detect the presence of specific ligands at or above their respective threshold concentrations, the reaction mixture is contacted with a terminal solid phase containing discrete zones of immobilized ligand receptors for the respective ligands and a signal development phase in order to determine which if any of the ligands were present at or above their threshold concentrations.

Furthermore, since each ligand receptor immobilized on the terminal solid phase is placed in a discrete locus or loci, the signal produced by the signal development element of an immobilized ligand analogue conjugate can be uniquely associated with a specific target ligand. The one-for-one association of detectable signal with ligand is achieved by correlating signal location with the positional identification of specific ligand receptors. The present invention, therefore, affords the concentration of a multiplicity of target ligands to be simultaneously assessed, each with respect to an individually preselected threshold concentration, such that the absence of a detectable signal in a ligand-specific reaction zone on the terminal solid phase indicates that the specific target ligand is present in the sample at a concentration less than the ligand-specific threshold concentration, while the presence of a detectable signal in a ligand-specific reaction zone on the terminal solid phase indicates that the specific ligand is present in the sample either at a concentration substantially equivalent to or greater than the ligand-specific threshold concentration.

Ligand-Receptor Assay Process for the Simultaneous Determination of Multiple Ligands With Multiple Threshold Concentrations for Each Ligand One of the embodiments of this invention is a ligand-receptor assay for a multiplicity of target ligands in which the reaction phase includes groups of complementary reagents, each group having multiple ligand analogue-ligand complement conjugates and an appropriate ligand receptor. The ligand analogue-ligand complement conjugates are constituted in proportions relative to the complementary reaction phase ligand receptor, such that at the complexation step with their respective terminal solid phase immobilized ligand complement receptors, signal development occurs so that each complementary ligand analogue-ligand complement conjugate::immobilized ligand complement receptor pair exhibits a unique threshold concentration for the commonly shared target ligand. The compendium of threshold concentrations for a single target ligand provides a mechanism for further identifying the concentration of the target ligand by comparison with the range of threshold concentrations. Since the reaction phase includes a multiplicity of groups of complementary reagent pairs, a multiplicity of target ligands may be simultaneously determined, each ligand having an associated series of threshold concentrations. Thereby in this fashion, each target ligand can be bracketed into one of a series of concentration ranges. Examples of such uses of ligand analogue-ligand complement conjugates to determine multiple analytes at multiple threshold levels include the use of ligand analogue-ligand complement conjugates in which the ligand complement component of the conjugate is sterically hindered from binding to the terminal solid phase ligand complement receptor upon the complexation of ligand receptor with the ligand analogue component of the ligand analogue-ligand complement conjugate. Such conjugates are described in U.S. Pat. No. 4,506,009. A reaction mixture which includes sample, ligand receptor and ligand analogue-ligand complement conjugate is allowed to substantially approach equilibrium. The reaction mixture is then contacted with a terminal solid phase upon which is localized ligand complement receptor. Ligand analogue-ligand complement conjugate:ligand receptor complex cannot be bound by terminal solid phase immobilized ligand complement receptor since the conjugate complex has an effective ligand complement concentration of zero. Unbound ligand analogue-ligand complement conjugate can be bound by the immobilized ligand complement receptor and following any necessary free/bound separation steps and contact with a signal development phase, the ligand concentration can be determined relative to the threshold concentration. When multiple ligand complement receptors are immobilized at specific loci on the terminal solid phase, each locus is identified with a unique threshold concentration such that the presence of a detectable signal at a locus indicates that the ligand is present in the sample at a concentration substantially equivalent to or greater that the corresponding threshold concentration.

Another example involves using a ligand analogue-ligand complement conjugate in the reaction mixture and the use of an optional means. A reaction mixture is formed from a sample, ligand receptor and a ligand analogue-ligand complement conjugate. The competition reaction between ligand and ligand analogue-ligand complement conjugate for the limited binding sites on the ligand receptor is allowed to substantially approach equilibrium. The reaction mixture then is contacted with an optional means operatively associated with a (ligand receptor) receptor which can bind to those components of the reaction mixture associated with ligand receptor, that is, unbound ligand receptor, ligand:ligand receptor complex, and ligand analogue-ligand complement conjugate:ligand receptor complex. The resulting reaction mixture then is contacted with a terminal solid phase upon which is immobilized ligand complement receptor. A portion of the unbound ligand analogue-ligand complement conjugate remaining in the reaction mixture is bound by the terminal solid phase immobilized ligand complement receptor and the remainder may be removed, if necessary, in a separation step. Finally, the terminal solid phase is contacted with a signal development phase and the ligand concentration is determined relative to the threshold concentration. When multiple ligand complement receptors are immobilized at specific loci on the terminal solid phase, each locus is identified with a unique threshold concentration such that the presence of a detectable signal at a locus indicates that the ligand is present in the sample at a concentration substantially equivalent to or greater that the corresponding threshold concentration.

Ligand-Receptor Assay Using Receptor Conjugate and Ligand Analogue Construct

One skilled in the art will appreciate that a receptor conjugate and a ligand analogue construct can be used in a reaction mixture to provide threshold concentrations for the determination of target ligands in ligand-receptor assays. Substantially all of the receptor conjugate is bound to ligand analogue construct and is prevented from binding to a terminal solid phase containing immobilized ligand analogue when the target ligand is present at less than the threshold concentration. Receptor conjugates containing multiple ligand binding sites are preferred for use in this embodiment. A ligand analogue construct can be formed by binding ligand analogue to an optional solid phase as a means for separating receptor conjugate from the reaction mixture. Alternatively, ligand analogue constructs can be formed by binding ligand analogues to large molecular species which will prevent receptor conjugates bound to such soluble ligand analogue constructs from binding to immobilized ligand analogue on the terminal solid phase without utilizing a means to separate the soluble ligand analogue constructs from the reaction mixture. One skilled in the art will appreciate that the present invention contemplates this use of receptor conjugates and ligand analogue constructs for the detection of single or multiple target ligands.

Assay for Ligand Receptor Using Receptor Conjugate and Ligand Analogue Construct One skilled in the art will appreciate that ligand receptors can be the target analyte of interest. In this case receptor conjugate and a ligand analogue construct are provided in the reaction phase such that when sample suspected of containing target ligand receptor is added to form the reaction mixture, substantially all of the receptor conjugate is bound to ligand analogue construct and is prevented from binding to a terminal solid phase containing immobilized ligand if the reaction mixture contains ligand receptor at less than the threshold concentration of the assay. The amounts of receptor conjugate and ligand analogue construct are selected to provide a predetermined threshold ligand receptor concentration for the assay. One skilled in the art will appreciate that the present invention contemplates an assay for multiple ligand receptors by providing a complementary pair of receptor conjugate and ligand analogue construct and a discrete zone of immobilized ligand analogue on the terminal solid phase for each target ligand receptor.

While the present invention is particularly useful for the performance of competitive immunoassays, those skilled in the art will appreciate that the invention may be utilized for other ligand-receptor assays, including non-competitive immunoassays. In sandwich assays, for example, a ligand receptor can be provided together with a ligand receptor conjugate which binds to a different site on the ligand molecule in a reaction mixture. When sample suspected of containing ligand is added to the reaction phase, the binding of ligand receptor, ligand receptor conjugate, and ligand is allowed to achieve substantially equilibrium binding. The amount of ligand receptor is selected to bind a predetermined amount of ligand such that when the reaction mixture is contacted with a solid phase containing immobilized ligand receptor, a known quantity of ligand receptor:ligand:ligand receptor conjugate complex is prevented from binding to the solid phase and therefore no response is developed until the ligand concentration in the sample exceeds a selected threshold concentration.

Examples of ligands which would serve as suitable targets for the present invention include the following; ovulatory steroids and their metabolites: e.g., progesterone, estradiol, pregnanediol-3α-glucuronide, and estrone-3-glucuronide; drugs of abuse and their metabolites: e.g., amphetamine, barbiturates, benzodiazepines, cannabinoids, cocaine, methadone, methamphetamine, methaqualone, opiates, phencyclidine, propoxyphene, and tricyclic antidepressants; therapeutic drugs and their metabolites: e.g., acetaminophen, digoxin, salicylate and theophylline; ovulatory hormones: e.g., human chorionic gonadotropin, and luteinizing hormone; thyroid hormones: e.g., triiodothyronine and thyroxine; mycotoxins: e.g., aflatoxin B1, aflatoxin B2, aflatoxin G1, aflatoxin M1, zearalenone, T-2 toxin, and deoxynivalenol; ciguatoxin; environmental toxins: e.g., polychlorinated biphenyls, dioxin, and ethylene dibromide; and proteins and antibodies of value in nosology: e.g., apolipoproteins, albumin, c-reactive protein and antibodies to hepatitis and HIV viruses. The following examples are offered by way of illustration and not by way of limitation.

EXAMPLE 1

Preparation of the N-Hydroxysuccinimide Ester of Estrone-3-Glucuronide

Estrone-3-glucuronide (11.2 mg, 25 µmol) and N-hydroxysuccinimide (2.9 mg, 25 µmol) were dissolved in 0.1 mL dry dimethylformamide. Dicyclohexylcarbodiimide (5.7 mg, 27.5 µmol) was added and the flask was purged with nitrogen. The reaction was stirred at room temperature or 3 hours. The reaction mixture was filtered on a small fritted funnel to remove the precipitated dicyclohexylurea. The resulting N-hydroxysuccinimide ester was used immediately for conjugation to protein.

Preparation of Estrone-3-Glucuronide Alkaline Phosphatase Conjugate

A solution of the N-hydroxysuccinimide ester of estrone-3-glucuronide (114 µl, 230 mM) in dimethylformamide was added to a solution of alkaline phosphatase (0.26 ml, 9.8 mg/ml) in 0.1M potassium borate, 0.05M potassium phosphate, 0.15M sodium chloride, pH 8.75. The reaction mixture was stirred at room temperature for 12 hours. The estrone-3-glucuronide alkaline phosphatase conjugate was purified by chromatography on a Sephadex G-25 column.

Preparation of Latex-Immobilized Affinity-Purified Goat IgG Antibody Against the Fc Fragment of Mouse IgG Affinity-purified goat-anti-mouse Fc (Immunosearch) and polystyrene latex particles (sulfated, 1.07 µm) (Interfacial Dynamics) were incubated separately at 45° C. for one hour, the antibody solution being buffered with 0.1M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in PBS containing 0.1% sodium azide at pH 7.0 at a latex concentration of 1% solids. This preparation was used to determine the immunoreactivities of conjugates and as an optional means for the removal of monoclonal antibody from the reaction mixture in the assay of estrone-3-glucuronide. A 1% suspension of this latex preparation was capable of binding 40 µg/ml of monoclonal antibody.

Measurement of Conjugate Immunoreactivity

In order to determine the fraction of ligand analogue conjugate that could bind to antibody, monoclonal antibody specific for the target ligand was incubated with a quantity of ligand analogue conjugate such that sufficient antibody was available to bind to all conjugates that had bindable ligand attached. A quantity of goat-anti-mouse Fc latex was added in sufficient quantity to completely bind all of the monoclonal antibody together with any conjugate bound to it. The latex was separated from the mixture by centrifugation and the amount of enzyme activity remaining in the supernatant was assayed and compared to the total amount of enzyme activity added to the mixture. The percentage of immunoreactive conjugate was the percentage of total enzyme activity that was bound to the latex pellet. Conjugates which exhibited high immunoreactivities were representative of conjugates that were highly derivatized with ligand analogues while conjugates with low immunoreactivities were representative of conjugates that were less highly derivatized.

Assay for Estrone-3-Glucuronide Using an Optional Means for Removal of Antibody From the Reaction Mixture A conjugate of estrone-3-glucuronide and alkaline phosphatase was prepared and its immunoreactivity was determined as described above using a monoclonal antibody, clone #27, obtained from Interpharm Laboratories, Rehovot, Israel. The conjugate was found to be 99.9% immunoreactive indicating that the enzyme was highly derivatized. Standards of estrone-3-glucuronide were prepared from dilutions of a 1 mM stock solution that was prepared by solubilization of a weighed quantity of estrone-3- glucuronide. Mixtures of the standards and the conjugate were prepared and 100 µl of each mixture was added to an equal volume of the monoclonal antibody at a concentration of 10 µg/ml in a suspension of 0.5% goat-anti-mouse Fc latex in microtiter plate wells. The mixtures, containing a final conjugate concentration of 4 nM and a final antibody concentration of 31 nM, were incubated for five minutes with gentle shaking before being subjected to centrifugation to pellet the latex. Fifty microliters of the supernatant from each well was added to microtiter plate wells containing immobilized monoclonal antibody, clone #27 (COBIND plates, Micro Membranes, antibody immobilized at 100

μg/ml using protocol specified by manufacturer) and incubated for 30 minutes at room temperature with gentle shaking. The wells were washed five times with borate buffered saline, pH 8.2, and the presence of bound enzyme activity was determined by adding 200 μl of 10 mM phenolphthalein monophosphate, buffered by 2-amino-2-methyl-1-propanol at pH 10.2, and kinetically measuring the formation of phenolphthalein at 560 nm using a UV max microtiter plate reader (Molecular Devices). In addition, the enzyme activity remaining in the supernatant was determined by removing 10 μl of the supernatant after pelleting the latex, adding it to 200 μl of 10 mM phenolphthalein monophosphate, and kinetically measuring the rate of formation of phenolphthalein at 560 nm as described. The results are shown in Table I in relation to the concentration of estrone-3-glucuronide in the reaction mixture. The results clearly show that until the concentration of estrone-3-glucuronide reaches 30 nM, both the enzyme activity bound to anti-estrone-3-glucuronide in the wells and the enzyme activity in the supernatant remain at very low levels. The immunoreactive conjugate is substantially all bound to the antibody in the reaction mixture until the concentration of estrone-3-glucuronide exceeds the threshold concentration of the assay which in this case is approximately 30 nM. The enzyme activity bound to the immobilized antibody in the microtiter plate wells reaches a maximum before the free enzyme activity in the supernatant reaches a maximum because the amount of immobilized antibody in the wells is insufficient to bind all of the available conjugate in the presence of the concentrations of free estrone-3-glucuronide used here. The results indicate that a terminal solid phase with a higher potential capacity for the immobilization of antibodies would improve the dynamic range of response of this assay.

TABLE I

| [Estrone-3-Glucuronide (nM) | Enzyme Activity Bound to Terminal Solid (mOD/min) | Enzyme Activity in Supernatant (mOD/min) |
| --- | --- | --- |
| 0 | 0.3 | 0.8 |
| 10 | 0.4 | 0.6 |
| 20 | 0.4 | 0.4 |
| 30 | 5.3 | 2.6 |
| 40 | 4.1 | 3.1 |
| 50 | 2.7 | 3.5 |
| 60 | 4.8 | 5.5 |
| 70 | 6.8 | 6.7 |
| 80 | 12.6 | 9.4 |
| 90 | 10.2 | 9.2 |
| 100 | 10.2 | 10.6 |
| 200 | 18.8 | 23.3 |
| 500 | 16.8 | 37.1 |
| 1000 | 13.5 | 46.8 |

Assay for Estrone-3-Glucuronide Using a Membrane as a Terminal Solid Phase

Monoclonal antibody to estrone-3-glucuronide, clone 155B3 from Interpharm Laboratories, was immobilized on 16-well microtiter plates that containe IMMOBILON membrane as the bottom element of the wells (Millipore Corporation). The antibody was spotted onto each membrane-well by applying 0.6 μl of a solution containing 6 mg/ml antibody, 0.1M potassium phosphate, 10 mg/ml tetrazole, and 0.1% polyvinyl alcohol (average molecular weight=2000), pH 7.4, and incubated for 20 minutes at room temperature before applying 20 μl of a solution containing 10 mg/ml casein, 0.1M potassium phosphate, 10 mg/ml tetrazole, and 0.1% polyvinyl alcohol, pH 7.4, and incubating for 5 minutes. The excess solution was blotted with absorbent paper and the plates were dried in a desiccated container before use in assays as the terminal solid phase.

Assays were performed by mixing equal volumes of estrone-3-glucuronide standards and estrone-3-glucuronide-alkaline phosphatase conjugate and adding to these mixtures an amount of anti-estrone-3-glucuronide antibody selected so that the concentration range spanned by the standards included the expected threshold concentration determined by the selection of the antibody concentration. The total reaction volume was 60 μl for each mixture. After 10 minutes of incubation, 20 μl was removed from each reaction mixture and was added to the wells containing antibody immobilized on membranes. The membranes remained in contact with the reaction mixture for approximately one minute before each well was washed by vacuum-assisted filtration of three 200 μl volumes of borate-buffered saline containing 0.05% LUBROL PX at pH 8.2. The wells were rinsed by vacuum-assisted filtration of 50 μl of substrate solution containing 10 mM phenolphthalein monophosphate at pH 10.2. The wells were blotted by contacting the bottoms of the wells with absorbent paper and 50 μl of the same substrate solution was added to each well. The rate of formation of phenolphthalein was kinetically measured using a UV max microtiter plate reader (Molecular Devices) at 560 nm. When the instrument reading was complete, the wells were washed with 50 μl of a substrate solution containing 10 mM 5-bromo-4-chloro-3-indoxyl phosphate (BCIP) at pH 10.2, the wells were blotted with absorbent paper, and 50 μl of BCIP substrate was added to develop a visual assay response. After approximately 10 minutes, the reactions were stopped adding 50 μl of 500 mM EDTA and blotting excess fluids from the membranes. The visual responses were compared to i.e. instrumental measurements to confirm the development of specific signals; both visual and instrumental responses were in agreement for the assays described here and no visual response was detected for wells where the concentration of estrone-3-glucuronide was below the threshold concentration. The results of two such assays, one using highly derivatized conjugate that exhibited an immunoreactivity of 90% and another using a sparsely derivatized conjugate exhibiting an immunoreactivity of 26%, are shown in Table II. The highly derivatized conjugate exhibited a threshold concentration of approximately 100 nM in this assay with a gradual increase in response up to a maximum reached at approximately 1000 nM. The assay utilizing the conjugate with 26% immunore-activity exhibited a threshold concentration of approxi-mately 120 nM and an assay response that increased more rapidly as a function of ligand concentration. We have found that the degree of derivatization as measured by the percentage immunoreactivity for the conjugate is a good predictor of the assay characteristics that will be exhibited by a particular conjugate. Highly derivatized conjugates result in assays that exhibit lower response slopes than less derivatized conjugates. This property can be used by one skilled in the art to optimize an assay for a specific application.

TABLE II

| [Estrone-3-Glucuronide 25 (nM) | 90% Immunoreactive Conjugate. Enzyme Activity Bound To Terminal solid Phase (mOD/min) | 26% Immunoreactive Conjugate. Enzyme Activity Bound To Terminal Solid Phase (mOD/min] |
| --- | --- | --- |
| 0 | 0.0 | 0.0 |
| 20 | 0.0 | 0.0 |
| 40 | 0.1 | 0.0 |
| 60 | 0.0 | 0.0 |
| 80 | 0.0 | 0.1 |
| 100 | 0.2 | 0.1 |
| 120 | 0.3 | 0.4 |
| 140 | 0.3 | 1.0 |

TABLE II-continued

| [Estrone-3-Glucuronide 25 (nM) | 90% Immunoreactive Conjugate. Enzyme Activity Bound To Terminal solid Phase (mOD/min) | 26% Immunoreactive Conjugate. Enzyme Activity Bound To Terminal Solid Phase (mOD/min] |
|---|---|---|
| 160 | 0.9 | 2.9 |
| 180 | 1.2 | 4.0 |
| 200 | 1.6 | 4.3 |
| 1000 | 17.0 | 18.9 |

Determination of the Approach to Equilibrium in an Assay for Estrone-3-Glucuronide In order to determine the incubation time needed for the reaction mixture to approach substantially equilibrium binding conditions, the most important parameter to examine is the assay response in the immediate vicinity of the threshold concentration because the approach to equilibrium is slowest at these concentrations of target ligand. A useful method is to perform the assay using target ligand concentrations above and below the threshold concentration and to examine the effect of variation in the incubation time of the reaction mixture on the assay response at these concentrations. The assay for estrone-3-glucuronide was performed as described in the previous example using a membrane as the terminal solid phase and the conjugate exhibiting 26% immunoreactivity, and using estrone-3-glucuronide standards such that the concentration in the reaction mixture was either 100 or 140 nM, bracketing the observed threshold concentration of 120 nM. The reaction mixtures were incubated for 1, 3, 6 or 10 minutes to determine the minimum time necessary to approach substantially equilibrium binding conditions. The results shown in Table III indicate that an incubation time of six minutes is sufficient so that no visually detectable signal is observed in assays containing 100 nM estrone-3-glucuronide while the assay response of assays containing 140 nM remains visually detectable.

TABLE III

| Reaction Mixture (mOD/min) | Enzyme Activity Bound to Terminal Solid Phase | |
|---|---|---|
| Incubation Time (min) | 100 nM | 140 nM |
| 1 | 0.6 | 2.5 |
| 3 | 0.3 | 1.4 |
| 6 | 0.05 | 1.1 |
| 10 | 0.0 | 0.5 |

EXAMPLE 2

Preparation of the N-Hydroxysuccinimide Ester of 5β-Pregnane-3α,20α-Diol Glucuronide Pregnanediol glucuronide (13.3 mg, 25 µmol) and N-hydroxysuccinimide (2.9 mg, 25 µmol) were dissolved in 0.1 mL dry dimethylformamide. Dicyclohexylcarbodiimide (5.7 mg, 27.5 µmol) was added and the flask was purged with nitrogen. The reaction was stirred at room temperature for 3 hours. The reaction mixture was filtered on a small fritted funnel to remove the precipitated dicyclohexylurea and the solvent was removed in vacuo. Anhydrous methanol was added to the residue and the flask was placed at -20° C. to precipitate the N-hydroxysuccinimide ester. The resulting crystals (12 mg) were isolated, dried, and stored desiccated at -20° C.

Preparation of Pregnanediol-3α-Glucuronide Alkaline Phosphatase Conjugate

The N-hydroxysuccinimide ester of pregnanediol glucuronide was dissolved in dry acetonitrile and reacted with alkaline phosphatase at 8 mg/ml protein using a tenfold molar excess of the N-hydroxysuccinimide ester. The reaction was performed in phosphate-buffered-saline at a pH of 7.0 for 90 minutes. The protein was removed from reactants by G-25 chromatography and its immunoreactivity was measured as described above and found to be 96%.

Assay for Prednanediol-3α-Glucuronide Using a Membrane as a Terminal Solid Phase A monoclonal antibody for pregnanediol-3α-glucuronide (clone P44, Interpharm Laboratories) was immobilized on immobilon membranes in 16-well microtiter plates as described above except that the antibody concentration used for immobilization was 16 mg/ml. Assays were performed by mixing equal volumes of pregnanediol-3α-glucuronide standards and pregnanediol-3α-glucuronide-alkine phosphatase conjugate and adding to these mixtures an amount of anti-pregnanediol-3α-glucuronide antibody selected so that the concentration range spanned by the standards included the threshold concentration determined by the selection of the antibody concentration. The total reaction mixture volume was 60 µl for each mixture. The reaction mixture was incubated for 10 minutes and all remaining assay procedures were performed as described above in the assays for estrone-3-glucuronide. The results are shown in Table IV and reflect a threshold concentration of approximately 3 µM for the first visually detectable result. The results further exhibit a "hook" effect that can be observed in such immunoassays where the combination of free ligand and free ligand analogue conjugate in the reaction mixture is in substantial excess over the amount of immobilized receptor on the terminal solid phase. When the maximum assay response, developed in this assay at approximately 50 µM, is compared to the maximum potential response that could be achieved if all of the free ligand analogue conjugate were bound to the terminal solid phase (determined by contacting reaction mixture containing conjugate only with the terminal solid phase), only 4% of the potentially available response is achieved in this assay. The use of terminal solid phases with increased amounts of immobilized antibody, the use of highly derivatized conjugates that can compete effectively with ligand for binding sites on the terminal solid phase, and the use of high concentrations of ligand analogue conjugate are all effective ways of improving the maximum response in assays where the threshold concentration is high so that the danger of a substantial "hook" effect is minimized. The combination of these parameters that is used to optimize an assay is understood by those skilled in the art to be dependent on the objectives of a particular immunoassay application.

TABLE IV

| [Pregnanediol-3α-Glucuronide] (µM) | Enzyme Activity Bound To Terminal Solid Phase (mOD/min) |
|---|---|
| 0 | 0.0 |
| 1 | 0.1 |
| 2 | 0.3 |
| 3 | 0.9 |
| 4 | 1.6 |
| 5 | 2.7 |
| 6 | 2.9 |
| 7 | 2.7 |
| 8 | 3.9 |

TABLE IV-continued

| [Pregnanediol-3α-Glucuronide] (μM) | Enzyme Activity Bound To Terminal Solid Phase (mOD/min) |
| --- | --- |
| 9 | 4.7 |
| 10 | 4.1 |
| 20 | 4.8 |
| 50 | 6.5 |
| 100 | 4.5 |

EXAMPLE 3

Simultaneous Multiple Assay for Drugs of abuse

The following example illustrates the application of the invention to an assay for a drugs of abuse panel. A drugs of abuse panel useful for screening urine samples would include the five drugs considered of greatest importance by the National Institute of Drug Abuse, (NIDA), amphetamine, cocaine, opiates, phencyclidine, and cannabinoids. Development of antibodies for these haptens requires the synthesis of immunogens. Methods for the synthesis of such immunogens are known to those skilled in the art, see for example, U.S. Pat. Nos. 3,817,837, 3,878,187, 3,884,898, 4,203,802 and 4,281,065, and Rodgers, R., Crowl, C. P., Eimstad, W. M., Hu, M. W., Kam, J. K., Ronald, R. C., Rowley, G. L., and Ullman, E. F., Clin. Chem., 24, 95–100 (1976). The immunogens produced by said methods are then used to immunize mice for the purposes of eliciting an immune response to the desired drugs. Subsequent to the elicitation of an immune response, the mice are sacrificed and the spleen cells are fused with myeloma cells to produce antibody secreting hybridoma cell lines. Further characterization of the antibodies derived from the cell lines is achieved by utilizing the immunogens used in the immunization protocols. The methods for producing and characterizing monoclonal antibodies are well known to those skilled in the art, see for example, Liu, D., Purssell, R., and Levy, J. G., Clinical Toxicology, 25, 527–538 (1987). The drugs and chemistry used in the creation of immunogens are also used in the synthesis of drug-enzyme conjugates which consist of enzymes such as calf intestine alkaline phosphatase derivatized with target drugs. Methods for the preparation of such drug derivatized enzymes are known to those skilled in the art, see for example, U.S. Pat. Nos. 3,817,837 and 4,203,802.

A reaction phase is constructed from appropriate amounts of the drug-enzyme conjugates and the monoclonal antibodies directed against the NIDA drug panel. The amounts of the antibodies are selected such that the assay determined threshold drug concentrations are consistent with the NIDA recommendations for the screening of positive from negative samples. Those threshold concentrations are amphetamine, 1000 ng/ml, cannabinoids, 100 ng/ml, cocaine, 300 ng/ml, opiates, 300 ng/ml, and phencyclidine, 25 ng/ml. The sample is mixed with the reaction phase to form a reaction mixture, which is allowed to react until the multiple competition reactions have substantially approached equilibrium binding conditions. The reaction mixture is then placed in contact with a test device which comprises in part a membrane upon which has been immobilized anti-drug antibodies in separate discrete reaction zones. The number of anti-drug reaction zones matches the number of drug-enzyme conjugate::anti-drug antibody pairs. Methods for the immobilization of antibodies upon membranes are well known to those skilled in the art, see for example Pluskal, M. G., Przekop, M. B., Kavonian, M. R., Vecoli, D., Hicks, D. A., BioTechniques, 4, 272–283 (1986). Drug-enzyme conjugate which was unbound to soluble anti-drug antibody at the completion of the reaction in the reaction mixture, then complexes with anti-drug antibody immobilized in the drug specific reaction zone on the membrane. A wash solution is used to separate any remaining free drug-enzyme conjugate in the reaction mixture from the membrane bound drug-enzyme conjugate. The membrane is then contacted with a solution containing an appropriate enzyme substrate capable of developing a visible color, e.g., for calf intestine alkaline phosphatase a solution containing 3-indoxyl phosphate would be suitable. Color development is allowed to occur and the response of each reaction zone is interpreted such that the absence of detectable color indicates that the drug targeted by that zone is at a concentration less than the threshold concentration, while the presence of detectable color indicates that the target drug is present at a concentration substantially equivalent to or greater than the threshold concentration. Each reaction zone is individually interpreted thus allowing all five target drugs to be assessed as positive or negative relative to the NIDA specified threshold concentrations.

EXAMPLE 4

Preparation of 3-O-Carboxymethylmorphine Hydrochloride

Morphine sulfate (1.67 g, $5\times10^{-3}$ mol) was dissolved with potassium carbonate (2.07 g, $1.5\times10^{-2}$ mol) in 80 ml ethanol. The solution was heated to reflux while stirring and a solution containing bromoacetic acid (0.7 g, $5\times10^{-3}$ mol) was added in 2 ml ethanol. This was refluxed for two hours, then the flask was cooled in an ice water bath. The pH was adjusted to 3 with 12N hydrochloric acid and precipitates were filtered. Solvents were evaporated under vacuum and 10 ml ethanol was added to the residue. Precipitates were filtered and solvents evaporated under vacuum. The residue was recrystallized from water/acetone (10:90). Approximately 300 mg of product was recovered.

Preparation of 3-O-[2-(2-Amino-4-Thiolbutanoic Acid Thiolactone)-Acetamide]-Morphine Hydrochloride (Morphine HCTL)

Homocysteine thiolactone hydrochloride (120 mg, $7.8\times10^{-4}$ mol), 62 mg ($7.8\times10^{-4}$ mol) pyridine, and 296 mg ($7.8\times10^{-4}$ mol) 3-O-carboxymethylmorphine hydrochloride were dissolved in 5 ml dimethylformamide. Addition of 1 ml of a dimethylformamide solution containing 177 mg ($8.6\times10^{-4}$ mol) dicyclohexylcarbodiimide followed. The flask was purged with argon and the solution stirred at 25° C. for three hours. The solvent was evaporated under vacuum and 20 ml water was added to the residue. The solution was stirred for five minutes then the insoluble dicyclohexyl urea was filtered. The filtrate was washed with 10 ml methylene chloride. The pH of the aqueous layer was adjusted to 7 with an aqueous solution of saturated potassium carbonate. The aqueous solution was extracted six times with 10 ml methylene chloride. The combined organic extracts were dried with 2 g magnesium sulfate, filtered, and the solvent removed under vacuum. Ethanol (20 ml) was added to the residue and evaporated under vacuum to remove the pyridine. Ethyl acetate (10 ml) was added and insoluble precipitates were filtered. Ethereal hydrochloric acid (1M) was added to the solution while stirring until the pH was red to litmus. The white solid was filtered and washed with ethyl acetate. The product was dried under vacuum and the yield was 316 mg.

Preparation of Morphine-Alkaline Phosphatase Conjugate

Three mg ($6.9\times10^{-6}$ mol) of sulfo-SMCC (Pierce) was added to 2.2 ml of 4.9 mg/ml alkaline phosphatase in 0.1M potassium phosphate, 0.02M potassium borate, 0.15M sodium chloride, pH 7.5. The protein solution was stirred for one hour at 25° C., then protein was separated from unreacted sulfo-SMCC by gel filtration chromatography on a column containing 40 Ml of a gellulose gel filtration medium (GH-25 Amicon Corporation) equilibrated in 0.1M potassium phosphate, 0.02M potassium borate, 0.15M sodium chloride, pH 7.0. The protein fraction eluting from the column was collected. MorphineHCTL was hydrolyzed by adding 63 µl of 0.12M potassium carbonate, 0.6 mM EDTA in 40% methanol to 0.6 mg of morphine-HCTL. The solution stood at 25° C. for ten minutes, then 30 µl of the solution was added to 250 µl of the alkaline phosphatase derivatized with sulfo-SMCC (3.6 mg/ml) in 0.1 M potassium phosphate, 0.02M potassium borate, 0.15M sodium chloride, 0.4 mM magnesium chloride, pH 7.0. The solution was stirred for 30 minutes at 25° C. and the protein was separated from the unreacted reagents by gel filtration chromatography as described above. The protein fraction was collected and the conjugate was diluted for use in assays into a solution containing 1% bovine serum albumin, 1 mM magnesium chloride, 0.1 mM zinc chloride, 0.1% sodium azide, and 10 mM 3-(4-morpholino) propane sulfonic acid, pH 7.0.

Quantitative Assay for Morphine Using a Single Calibration Point

A conjugate of morphine and alkaline phosphatase was prepared and its immunoreactivity was determined as described above using a monoclonal antibody chosen for its high affinity to morphine. The conjugate was found to be >99% immunoreactive. A stock solution of morphine in buffer was prepared by solubilization of a weighed quantity of morphine in a known volume. A standard containing 1000 nM of morphine was prepared from the stock and further standards used in the assay were prepared from this standard by direct dilution. The assay was performed in a microtiter plate by adding to each well 25 µl of an antibody concentration that was chosen to provide a threshold concentration in the range of concentrations spanned by the standards. Standards containing 0, 60, 70, 80, 90, 100, 150, 200, 300, 400, and 500 nM morphine concentrations were added to the microtiter wells, 25 µl per well in replicates of six for each concentration used. The morphine-alkaline phosphatase conjugate was added in 25 µl volumes to each well at a final alkaline phosphatase concentration of approximately 1 nM. The reaction mixtures were incubated for 30 minutes at room temperature before 25 µl of a 1% suspension of goat-anti-mouse Fc latex was added and incubated for a further 5 minutes. The reaction mixtures were subjected to centrifugation to pellet the latex and 25 µl of the supernatant was removed from each well and assayed for enzyme activity by mixing it with 200 µl of 10 mM phenolphthalein monophosphate, buffered by 2-amino-2-methyl-1-propanol (AMP) at pH 10.2, and kinetically measuring the rate of formation of phenolphthalein at 560 nm as described. In order to determine the maximum potential response of the assay, six replicates were performed where assay diluent was substituted for the antibody solution so that the activity measured represented the total enzyme activity obtained when all of the conjugate is not bound by antibody. The ratio of free to bound activity for each standard concentration was determined by dividing the average response (free activity) by the difference between the average maximum response and the average response (bound activity). The ratio of free to bound as a function of the concentration of morphine in the sample was subjected to linear regression analysis for the standards that were above the threshold concentration that did not approach the maximum response where the error in the calculation of the ratio of free to bound becomes large. The standards at 60, 70, and 80 nM were found to be below the threshold concentration and did not generate assay responses that exceeded the background noise of the assay system. The standards at 300, 400, and 500 nM generated responses that were close to the maximum response yielding large errors in the calculation of the ratio of free to bound. The assay responses generated by the standards at 90, 100, 150, and 200 nM were used in the linear regression analysis to determine the linear dependence of the ratio of free to bound conjugate as a function of the morphine concentration. The slope of the line was found to be 29.346 units per µM and the intercept of the ratio of free to bound axis was -2.613 units. These parameters are constants of the assay system provided that the assay reagents and their volumes do not change. They can be used to determine the concentration of morphine in assays of samples by calculating the concentration of morphine from $$[\text{Morphine}] = \frac{(R_{fb} + 2.613)}{(29.346)}$$

where the ratio of free to bound is determined by dividing the assay response for the sample by the difference between the maximum response and the assay response. Using the individual responses obtained in this assay for the six replicates of the calibrator at 150 nM, maximum assay responses were determined. Each maximum assay response was then used to calculate the ratio of free to bound for each assay response for the 90, 100, and 200 nM standards and the corresponding concentration of morphine determined by the linear regression above. The precision and accuracy in determining the concentrations of the standards by this method is a good approximation of the performance of the assay system in determining unknown concentrations of morphine in samples. The results listed in Table V indicate that the assay is very precise in the quanititation of morphine concentrations in the range from 90 to 200 nM. It should be noted that the actual concentrations of the standards are not necessarily identical to the values assigned by the dilution of the stocks above. The useful range of the assay generally covers the range of 0.05 to 4 in the ratio of free to bound. The range of ligand concentration that corresponds to this range can be selected according to the goals of the assay system using methods described herein.

TABLE V

Quantitative Morphine Assay Using Single Calibration Point 150 nM

| Calibrator Response (mOD/min) | Maximum Response (mOD/min) | Calculated Response (mOD/min) | Calculated [Morphine] | Calculated Response (nM) | [Morphine] (mOD/min) | Response (nM) | [Morphine] (mOD/min) |
|---|---|---|---|---|---|---|---|
| 37.1 | 58.5823 | 5.2 | 92.36 | 14.4 | 100.15 | 44.9 | 200.87 |
|  |  | 3.7 | 91.34 | 12.7 | 98.47 | 45.6 | 208.73 |
|  |  | 5.9 | 92.86 | 13.6 | 99.34 | 45.2 | 204.14 |
|  |  | 5.0 | 92.22 | 13.5 | 99.25 | 45.5 | 207.56 |
|  |  | 5.5 | 92.57 | 13.3 | 99.05 | 45.7 | 209.93 |
|  |  | 4.3 | 91.74 | 10.9 | 96.83 | 45.0 | 201.94 |
|  | Mean |  | 92.18 |  | 98.85 |  | 205.53 |
|  | C.V. |  | 0.60% |  | 1.14% |  | 1.82% |
| 36.8 | 58.1086 | 5.2 | 92.39 | 14.4 | 100.27 | 44.9 | 204.88 |
|  |  | 3.7 | 91.36 | 12.7 | 98.57 | 45.6 | 213.27 |
|  |  | 5.9 | 92.89 | 13.6 | 99.45 | 45.2 | 208.36 |
|  |  | 5.0 | 92.25 | 13.5 | 99.35 | 45.5 | 212.01 |
|  |  | 5.5 | 92.60 | 13.3 | 99.16 | 45.7 | 214.54 |
|  |  | 4.3 | 91.76 | 10.9 | 96.91 | 45.0 | 206.02 |
|  | Mean |  | 92.21 |  | 98.95 |  | 209.85 |
|  | C.V. |  | 0.61% |  | 1.15% |  | 1.91% |
| 38.1 | 60.1614 | 5.2 | 92.27 | 14.4 | 99.76 | 44.9 | 189.30 |
|  |  | 3.7 | 91.27 | 12.7 | 98.16 | 45.6 | 195.75 |
|  |  | 5.9 | 92.75 | 13.6 | 98.99 | 45.2 | 191.99 |
|  |  | 5.0 | 92.13 | 13.5 | 98.90 | 45.5 | 194.79 |
|  |  | 5.5 | 92.47 | 13.3 | 98.71 | 45.7 | 196.73 |
|  |  | 4.3 | 91.66 | 10.9 | 96.58 | 45.0 | 190.18 |
|  | Mean |  | 92.09 |  | 98.52 |  | 193.12 |
|  | C.V. |  | 0.59% |  | 1.10% |  | 1.59% |
| 36.9 | 58.2665 | 5.2 | 92.38 | 14.4 | 100.23 | 44.9 | 203.51 |
|  |  | 3.7 | 91.35 | 12.7 | 98.54 | 45.6 | 211.72 |
|  |  | 5.9 | 92.88 | 13.6 | 99.42 | 45.2 | 206.92 |
|  |  | 5.0 | 92.24 | 13.5 | 99.32 | 45.5 | 210.49 |
|  |  | 5.5 | 92.59 | 13.3 | 99.12 | 45.7 | 212.96 |
|  |  | 4.3 | 91.76 | 10.9 | 96.88 | 45.0 | 204.63 |
|  | Mean |  | 92.20 |  | 98.92 |  | 208.37 |
|  | C.V. |  | 0.68% |  | 0.79% |  | 1.75% |
| 38.0 | 60.0035 | 5.2 | 92.27 | 14.4 | 99.80 | 44.9 | 190.34 |
|  |  | 3.7 | 91.28 | 12.7 | 98.19 | 45.6 | 196.92 |
|  |  | 5.9 | 92.76 | 13.6 | 99.03 | 45.2 | 193.09 |
|  |  | 5.0 | 92.14 | 13.5 | 98.93 | 45.5 | 195.94 |
|  |  | 5.5 | 92.48 | 13.3 | 98.75 | 45.7 | 197.92 |
|  |  | 4.3 | 91.67 | 10.9 | 96.61 | 45.0 | 191.25 |
|  | Mean |  | 92.10 |  | 98.55 |  | 194.24 |
|  | C.V. |  | 0.59% |  | 1.10% |  | 1.61% |
| 37.7 | 59.5298 | 5.2 | 92.30 | 14.4 | 99.91 | 44.9 | 193.62 |
|  |  | 3.7 | 91.30 | 12.7 | 98.28 | 45.6 | 200.59 |
|  |  | 5.9 | 92.79 | 13.6 | 99.13 | 45.2 | 196.53 |
|  |  | 5.0 | 92.17 | 13.5 | 99.04 | 45.5 | 199.55 |
|  |  | 5.5 | 92.51 | 13.3 | 98.84 | 45.7 | 201.64 |
|  |  | 4.3 | 91.69 | 10.9 | 96.68 | 45.0 | 194.58 |
|  | Mean |  | 92.13 |  | 98.65 |  | 197.75 |
|  | C.V. |  | 0.59% |  | 1.11% |  | 1.68% |
|  | Overall Mean |  | 92.15 |  | 98.74 |  | 201.48 |
|  | Overall C.V. |  | 0.56% |  | 1.02% |  | 3.80% |

EXAMPLE 5

Preparation of Morphine-Bovine Serum Albumin Conjugate

Seventy-five µl of a solution containing 20 mg of SMCC (Pierce) in 1 ml of acetonitrile was added to 1.9 ml of 20 mg/ml bovine serum albumin in 0.1M potassium borate, 0.1M potassium phosphate, 0.15M sodium chloride, pH 7.5. The solution was stirred for one hour at 25° C., then the protein was separated from the unreacted reagent by gel filtration chromatography on a column containing GH 25 (Amicon Corporation) equilibrated in 0.1M potassium phosphate, 0.02M potassium borate, 0.15M sodium chloride, pH 7.0. The protein fraction was collected. A volume of 0.42 ml of 0.12M potassium carbonate, 0.6 mM EDTA in 40% methanol was added to 4 mg morphine-HCTL. After ten minutes, 140 µl of the solution was added to 8.2 ml of the bovine serum albumin derivatized with SMCC (4.6 mg/ml). The solution was stirred for two hours at 25° C., then dialyzed in two liters of 10 mM (2-(N-morpholino)) ethane sulfonic acid, pH 5.0. The dialysis buffer was changed twice before collecting the morphine-BSA conjugate.

Preparation of Morphine-Colloidal Gold Conjugate

Colloidal gold with an average diameter of 45 nm was prepared according to the method of Frens, *Nature, Physical Sciences*, 241, 20 (1973). Morphine-colloidal gold conjugate was prepared by adding 5.6 ml of 0.1M (2-(N-morpholino) ethane sulfonic acid (MES), pH 5.8, dropwise to 50 ml of colloidal gold with rapid stirring. Morphine-BSA conjugate (3 mg/ml in 10 mM MES, 0.02% sodium azide, pH 5.8) was added in a bolus to the colloidal gold while stirring rapidly. After complete mixing the stirring was stopped and the solution incubated for 30 minutes at room temperature. The addition of 1 ml of BSA (3 mg/ml in 10 mM MES, 0.02% sodium azide, pH 5.8) with mixing and a five-minute incubation followed. Polyethylene glycol (average molecular weight=20,000) was added in a 1% solution (0.59 ml) and mixed. The colloidal gold was subjected to centrifugation at 27,000 g for 12 minutes at 4° C. to pellet it. The supernatant was removed and the pellet was washed twice with 35 ml of 10 mM potassium phosphate, 0.01% polyethylene glycol, 0.02% sodium azide, pH 7.0, by resuspending it and subjecting it to centrifugation as described. After the final centrifugation, the pellet was resuspended in 0.5 ml of the buffer and stored at 4° C.

Threshold Immunoassay for Morphine Using Morphine-Colloidal Gold Conjugate

Figure 7:
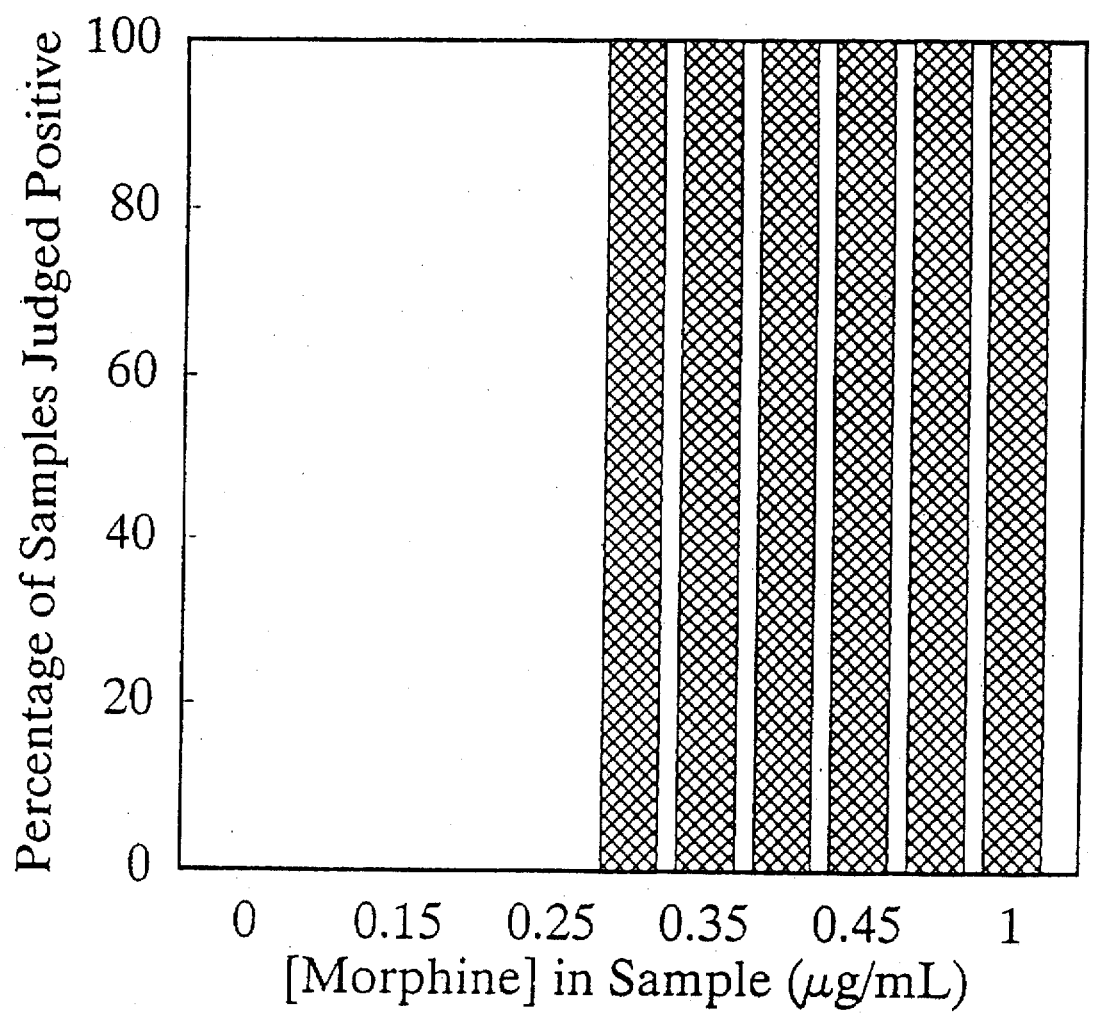
FIG. 7 is a graph showing the visually interpreted assay results from the assays of samples containing concentrations of morphine bracketing the threshold concentration. The graph shows that the assay can reliably detect concentrations of morphine at and above the threshold concentration.
Figure 8:
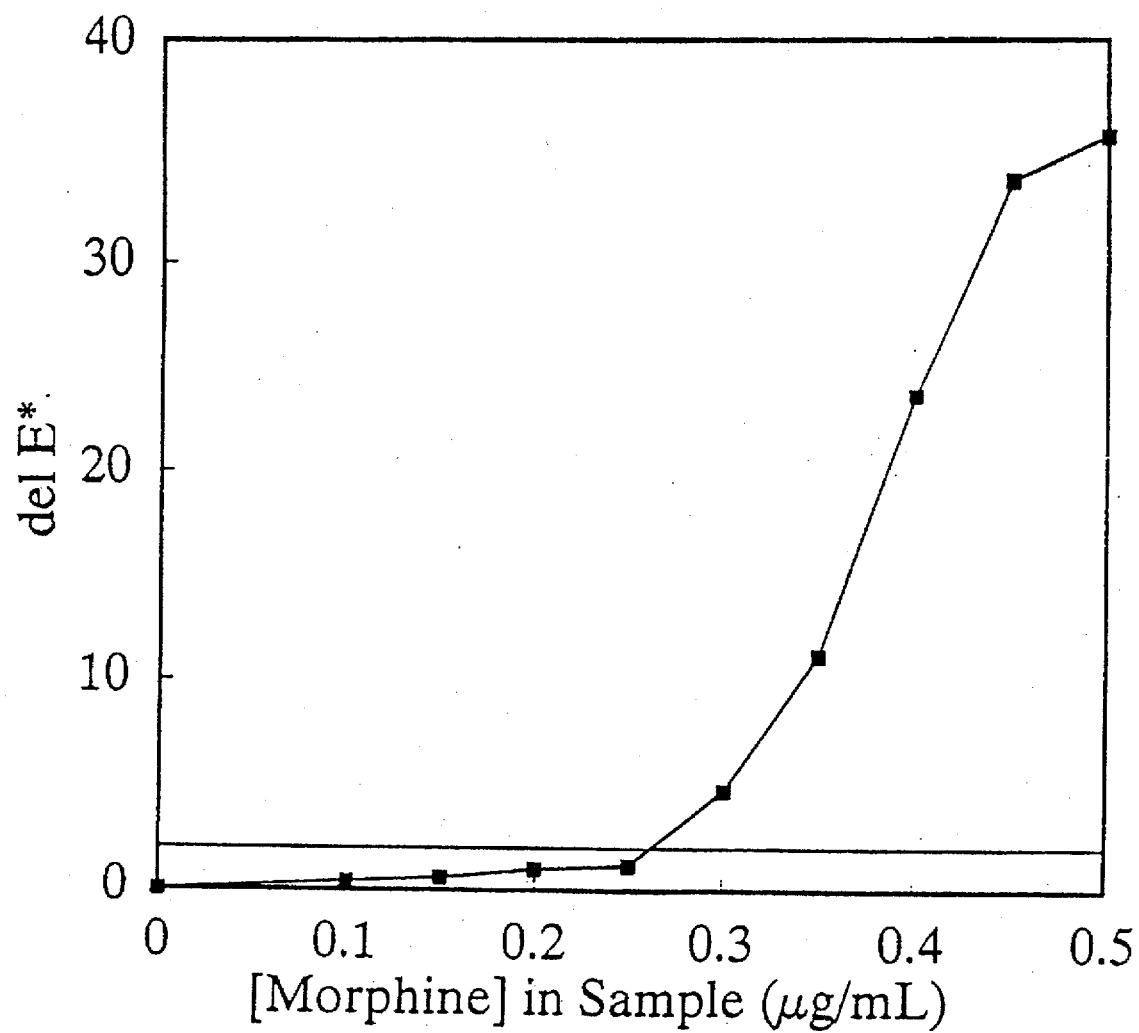
FIG. 8 is graph showing the assay response in units of the minimum detectable color difference that can be perceived by the human eye as a function of the morphine concentration in the sample. The graph shows that the color of the assay response first becomes visible (limit of visual detection shown as horizontal lines) at the threshold concentration and the assay response increases rapidly as a function of the morphine concentration in the sample.

An assay device incorporating a terminal solid phase was constructed using nylon membrane (Pall Biodyne C, 1.2μ pore size) by laminating the membrane to a polystyrene sheet of plastic that had 4 mm diameter holes punched in it and a pressure-sensitive adhesive (444 acrylic adhesive, 3M Company) on its surface. A monoclonal antibody to morphine was immobilized to the nylon membrane exposed in the holes in the polystyrene by adsorption. A 1 mg/ml solution of the antibody in buffer containing sodium citrate at 0.1M, pH 3.0, was applied to the membrane (6 μl per hole) and allowed to adsorb for a few minutes before a solution containing 0.5% casein, 0.5% BSA, 0.1M potassium phosphate, 10% sucrose, pH 7.0, was applied (10 μl per hole) in order to block the remaining sites of adsorption. Reagents and samples used in reaction mixtures were the morphine-colloidal gold conjugate described above diluted by a factor of 3 in 1% BSA, 0.1M potassium phosphate, 0.15M sodium chloride, 0.01M EDTA, 0.01% polyethylene glycol (average molecular weight =20,000), 0.02% sodium azide, pH 7.0 (hereafter referred to as diluent), a monoclonal antibody to morphine at 0.27 mg/ml in diluent, and morphine standards at 0.1, 0.15, 0.2, 0.25, 0.3, 0.35, 0.4, 0.45, and 0.5 μg/ml in urine. The standards were prepared by direct dilution from a 1 μg/ml solution in opiate-free urine. The 1 μg/ml solution was made from a 1 mg/ml stock prepared by dissolution of a weighed quantity of morphine sulfate. The assays were performed in microtiter plate wells by addition of 10 μl of the antibody solution, 20 μl of the sample, and 10 μl of the conjugate followed by an incubation of five minutes before contacting 20 μl of the reaction mixture with one of the nylon membranes containing immobilized antibody in the assay device. The membrane exposed in the hole was then contacted with absorbent paper from the bottom side so that the reaction mixture was drawn through the membrane and into the absorbent paper. Any conjugate not bound to the membrane was washed away by the addition of a drop of borate buffered saline containing 0.02% LUBROL, a non-ionic detergent, pH 8.0, while the membrane was in contact with the absorbent paper so that the wash solution was drawn through the membrane. The color remaining on the membrane was visually noted and was instrumentally measured using a Macbeth Color-eye at 540 nm. The data was transformed into units of E* which are a measure of the minimum color difference that can be perceived by the human eye. A more complete description of this unit of measure for color can be found in *Color in Business, Science and Industry* by D. B. Judd and G. Wyszecki, John Wiley and Sons. The assays were performed in a single-blind manner using coded samples in random order so that the concentrations of the samples were not known during the assay. A total of nine replicate assays were performed with each sample. An assay that resulted in a color that was visibly detectable above the background color of the membrane was judged to be positive. The results for the visual interpretation of the assays are summarized in FIG. 7. The results indicate that the assay can accurately determine the concentration of morphine in samples relative to the threshold concentration of 0.3 μg/ml. The instrumental measurement of the assay responses is summarized in FIG. 8. The first visual signal detectable above the background color of the membrane is shown to occur at 0.3 μg/ml and the color of the response is shown to rapidly increase above the threshold concentration.

EXAMPLE 6

Preparation of Estrone-3-Glucuron-(2-Amino-4-Thiolbutanoic Acid Thiolactone1)-Amide (E3G-HCTL)

77 mg ($1.7 \times 10^{-4}$ mol) of estrone-3-glucuronide, 29 mg ($1.9 \times 10^{-4}$ mol) of homocysteine thiolactone hydrochloride, and 0.015 ml ($1.9 \times 10^{-4}$ mol) of pyridine were dissolved in 0.47 mL of dimethylformamide. This mixture was added to a solution containing 30 mg ($1.9 \times 10^{-4}$ mol) dicyclohexylcarbodiimide in 0.23 mL of dimethylformamide. The flask was purged with argon, sealed and stirred at 25° C. for three hours. The insoluble precipitate was filtered and the solvent removed in vacuo. The residue was resuspended in 0.4 mL of an ethanol/water (15:12 v/v) solution and the insoluble precipitates removed by filtration.

The crude reaction mixture was then dissolved in 0.5 mL of an ethanol/water (15:12 v/v) solution and applied to a C18 HPLC column (1 cm×25 cm) equilibrated with a 1:9 mixture methanol/water using a flow rate of 2.0 mL/min. The compound was eluted with a gradient ramping from a 1:9 mixture of methanol/water to a 1:1 mixture of methanol/water in eight minutes, and was then ramped to a solution of 100% methanol in an additional 20 minutes. E3G-HCTL eluted between 25 and 27 minutes. The fractions containing product were combined and the solvents were removed in vacuo. 63 mg of E3G-HCTL were recovered.

Preparation of Alkaline Phosphatase-Estrone-3-Glucuronide

E3G-HCTL was hydrolyzed by placing 3 μl of a 210 mM E3G-HCTL methanol solution into 20 μl of a solution containing 0.12M $K_2CO_3$ and 0.6 mM EDTA in 40% methanol. After ten minutes at 25° C. the solution was added to 0.5 mL of a solution containing 1.8 mg/mL alkaline phosphatase-SMCC with 0.1M potassium phosphate, 0.02M potassium borate, 0.15M sodium chloride and 0.2 mM $MgCl_2$ at a pH of 7.0. The derivatization of alkaline phosphatase with sulfo-SMCC is described above in Example 4.

The reaction was stirred for three hours at 25° C. and then the resulting solution was chromatographed over a 14 mL column of GH 25 (Amicon) which had been equilibrated with a solution containing 0.1M potassium phosphate, 0.02M potassium borate and 0.15M sodium chloride at a pH of 7.0. The alkaline phosphatase-E3G conjugate eluent was collected and yielded 1.5 mL at a concentration of 0.16 mg/mL.

Preparation of the Solid Phase Laminate

Six 1.8"×2.0" sheets of nylon membrane (5.0 μm Pall BIODVNE C) were prepared by placing the sheets in 6 mL of a solution containing 0.41 mg/mL of an anti-E3G monoclonal antibody and 0.1M sodium citrate at a pH of 3.0. The solution was rocked for 1.5 hours at 25° C., and then the excess protein binding sites on the membranes were blocked by placing the membrane sheets into 20 mL of a solution containing 0.1M potassium phosphate, 0.1% w/v casein, 0.1% v/v Triton X-100 and 10% w/v sucrose at a pH of 7.0 and then allowing the sheets to soak for three minutes. The membranes were blotted dry and then placed in a vacuum desiccator overnight.

The membranes were cut into strips of 0.3"×2" and then affixed to a polystyrene strip (1"×3"×0.020") with doublesided adhesive (3M Co-444). The polystyrene strip and adhesive laminate had a 0.1"×1.5" slot cut into the middle of the two-layer laminate.

Assay For Estrone-3-Glucuronide Using a Laminate as a Solid Phase

The reaction mixtures were prepared by mixing samples containing estrone-3-glucuronide and alkaline phosphatase-E3G (AP-E3G) with an anti-E3G monoclonal antibody. Thus were prepared solutions containing 0.9 mg/mL AP-E3G, 0.18 mg/mL anti-E3G monoclonal antibody and E3G at the following concentrations: 0, 1 µm, 1.6 µM, 2.6 µM, 7.8 µM, 26 µM and 130 µM. The reaction mixtures were allowed to incubate for eight minutes at 25° C., after which 50 µl of the reaction mixture was applied to one end of the slot on the membrane/polystyrene laminate. The reaction mixture was allowed to migrate vertically up the membrane device. After migration of the reaction mixture was complete (within approximately 12 minutes) the membrane device was washed by placing the device in contact with an absorbent and washing with 0.5 mL of a solution containing 50 mM potassium borate, 0.15M NaCl and 0.05% v/v Lubrol. A 100 µl aliquot of an enzyme substrate solution containing 4 mg/mL indoxyl phosphate, 0.2M AMP, 0.5M Tris and 0.1% w/v sodium azide at a pH of 10.2 was then applied to the membrane and the enzyme allowed to turn over substrate for one minute. The substrate turnover step was quenched with a 300 µL aliquot of a solution containing 0.5M EDTA at a pH of 8.0. The length of the colored portion of the slot was measured and the results are tabulated in Table VI.

TABLE VI

| E3G (µM) | $R_f$ |
|---|---|
| 0.0 | 0.00 |
| 1.0 | 0.00 |
| 1.6 | 0.17 |
| 2.6 | 0.50 |
| 7.8 | 0.74 |
| 26.0 | 0.77 |
| 130.0 | 0.97 |

$R_f$ indicates the distance of travel of AP-E3G conjugate along the membrane as a function of the total distance of travel of the reaction mixture.

We claim:

1. Method for determining the presence of at least one target ligand, capable of competing with a ligand analogue conjugate for binding sites available on a ligand receptor, said ligand analogue conjugate comprising at least one ligand analogue coupled to a colloidal gold particle, in a fluid sample suspected of containing said target ligand comprising the steps of:

a. contacting said fluid sample with said ligand analogue conjugate and said ligand receptor to form a homogeneous reaction mixture, the relative amounts of said ligand analogue conjugate and said ligand receptor being selected such that in the absence of said target ligand and subsequent to substantially equilibrium binding in said reaction mixture, substantially all of said ligand analogue conjugate is bound to said ligand receptor such that no unbound ligand analogue conjugate is detected as a result of the assay method;

b. detecting unbound ligand analogue conjugates in said reaction mixture by visual means using at least one ligand receptor immobilized on a solid phase in at least one distinct locus;

c. relating the detectable signal to the presence of said target ligand in said fluid sample.

2. Method for determining the presence of at least one target ligand, capable of competing with a ligand analogue conjugate for binding sites available on a ligand receptor, said ligand analogue conjugate comprising at least one ligand analogue coupled to a colloidal gold particle, in a fluid sample suspected of containing said target ligand, comprising the steps of:

a. contacting said fluid sample with said ligand analogue conjugate and said ligand receptor to form a homogeneous reaction mixture, the relative amounts of said ligand analogue conjugate and said ligand receptor being selected such that in the absence of said target ligand and, subsequent to substantially equilibrium binding in said reaction mixture, substantially all of said ligand analogue conjugate is bound to said ligand receptor such that no unbound ligand analogue conjugate is detected as a result of the assay method;

b. removing ligand receptor from said reaction mixture;

c. detecting unbound ligand analogue conjugate in said reaction mixture by visual means using at least one ligand receptor immobilized on a solid phase in at least one distinct locus;

d. relating the detectable signal to the presence of said target ligand in said fluid sample.

3. Method for determining the presence of at least one target ligand at or above at least one predetermined threshold ligand concentration, said target ligand capable of competing with a ligand analogue conjugate for binding sites available on a ligand receptor, said ligand analogue conjugate comprising at least one ligand analogue coupled to a colloidal gold particle, in a fluid sample suspected of containing said target ligand comprising the steps of:

a. contacting said fluid sample with said ligand analogue conjugate and said ligand receptor to form a homogeneous reaction mixture;

(i) the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugate is detected as a result of the assay method; and (ii) the relative and absolute amounts of ligand analogue conjugate and ligand receptor being selected such that at least one of said predetermined threshold ligand concentration is established below which no unbound ligand analogue conjugate is detected as a result of the assay method;

b. detecting unbound ligand analogue conjugate in said reaction mixture by visual means using at least one ligand receptor immobilized on a solid phase in at least one distinct locus;

c. relating the detectable signal to the amount of said target ligand at or above said predetermined threshold ligand concentration in said fluid sample.

4. Method for determining the presence of at least one target ligand at or above at least one predetermined threshold ligand concentration, said target ligand capable of competing with a ligand analogue conjugate for binding sites available on a ligand receptor, said ligand analogue conjugate comprising at least one ligand analogue coupled to a colloidal gold particle, in a fluid sample suspected of containing said target ligand, comprising the steps of:

a. contacting said fluid sample with said ligand analogue conjugate and said ligand receptor to form a homogeneous reaction mixture;

(i) the relative amounts of said ligand analogue conjugate and said ligand receptor being selected such that in the absence of said target ligand, and subsequent to substantially equilibrium binding in said reaction mixture, substantially all of said ligand analogue conjugate is bound to said ligand receptor such that no unbound ligand analogue conjugate is detected as a result of the assay method; and (ii) the relative and absolute amounts of ligand analogue conjugate an ligand receptor being selected such that at least one of said predetermined threshold ligand concentration is established below which no unbound ligand analogue conjugate is detected as a result of the assay method;

b. removing ligand receptor from said reaction mixture;

c. detecting unbound ligand analogue conjugate in said reaction mixture by visual means using at least one ligand receptor immobilized on a solid phase in at least one distinct locus;

d. relating the detectable signal to the amount of said target ligand at or above said predetermined threshold ligand concentration in said fluid sample.

* * * * *